United States Patent
Gu et al.

(10) Patent No.: US 12,275,821 B2
(45) Date of Patent: Apr. 15, 2025

(54) REMOLDABLE BISMALEIMIDE RESIN AND APPLICATION THEREOF

(71) Applicant: SOOCHOW UNIVERSITY, Suzhou (CN)

(72) Inventors: Aijuan Gu, Suzhou (CN); Guozheng Liang, Suzhou (CN); Li Yuan, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 689 days.

(21) Appl. No.: 17/631,389

(22) PCT Filed: Jul. 28, 2020

(86) PCT No.: PCT/CN2020/105316
§ 371 (c)(1),
(2) Date: Jan. 28, 2022

(87) PCT Pub. No.: WO2021/018158
PCT Pub. Date: Feb. 4, 2021

(65) Prior Publication Data
US 2022/0348718 A1    Nov. 3, 2022

(30) Foreign Application Priority Data

Jul. 30, 2019 (CN) .......................... 201910696965.1

(51) Int. Cl.
*C08G 73/12* (2006.01)
*B29B 7/00* (2006.01)
(Continued)

(52) U.S. Cl.
CPC .............. *C08G 73/124* (2013.01); *B29B 9/02* (2013.01); *B29C 43/003* (2013.01); *B29C 43/52* (2013.01);
(Continued)

(58) Field of Classification Search
CPC ..... C07D 209/00; C08F 222/40; C08G 73/12; C08G 73/124
See application file for complete search history.

(56) References Cited

U.S. PATENT DOCUMENTS

2001/0020071 A1    9/2001   Capote et al.

FOREIGN PATENT DOCUMENTS

| CN | 106585047 A | 4/2017 |
| CN | 110330649 A | 10/2019 |
| WO | 2018091253 A1 | 5/2018 |

OTHER PUBLICATIONS

Guozheng Liang et al., "Modifier of bismaleimide (BMI): allyl compounds" New Chemical Materials, No. 3, p. 29 (Mar. 25, 1996).

*Primary Examiner* — Marc S Zimmer
*Assistant Examiner* — Surbhi M Du
(74) *Attorney, Agent, or Firm* — SZDC Law PC

(57) ABSTRACT

A remoldable bismaleimide resin and application thereof. The preparation method includes blending 2-allylphenyl glycidyl ether and terephthalic acid in acetonitrile, carrying out an esterification reaction under the condition of quaternary ammonium salt as a catalyst to obtain bis(3-(2-allylphenoxy)-2-hydroxypropyl) terephthalate containing a reversible dynamic group; then uniformly mixing bis(3-(2-allylphenoxy)-2-hydroxypropyl) terephthalate and bismaleimide, curing to obtain the re-moldable bismaleimide resin. The prepared re-moldable bismaleimide resin not only has excellent heat resistance and mechanical properties, but also can be remolded under hot pressing conditions. The preparation method of the re-moldable bismaleimide resin has the advantages of wide raw material sources and simple process, and has a wide application prospect in the fields of aerospace, transportation, electronic information, new energy, insulated electrical industry and the like.

10 Claims, 8 Drawing Sheets

(51) Int. Cl.
*B29B 7/82* (2006.01)
*B29B 9/02* (2006.01)
*B29C 43/00* (2006.01)
*B29C 43/52* (2006.01)
*B29K 96/00* (2006.01)
*C07D 209/00* (2006.01)
*C08F 222/40* (2006.01)
*C08G 59/14* (2006.01)
*C08J 5/24* (2006.01)
*C08L 79/08* (2006.01)

(52) U.S. Cl.
CPC .......... *C07D 209/00* (2013.01); *C08F 222/40* (2013.01); *C08F 222/408* (2020.02); *C08G 59/14* (2013.01); *C08G 73/12* (2013.01); *C08G 73/126* (2013.01); *C08J 5/24* (2013.01); *C08L 79/085* (2013.01); *B29B 7/002* (2013.01); *B29B 7/826* (2013.01); *B29K 2096/00* (2013.01); *C08F 2810/20* (2013.01); *C08G 2280/00* (2013.01); *C08L 2201/08* (2013.01); *C08L 2201/12* (2013.01)

REMOLDABLE BISMALEIMIDE RESIN AND APPLICATION THEREOF

This application is the National Stage Application of PCT/CN2020/105316, filed on Jul. 28, 2020, which claims priority to Chinese Patent Application No. 201910696965.1, filed on Jul. 30, 2019, which is incorporated by reference for all purposes as if fully set forth herein.

TECHNICAL FIELD

The present invention relates to a thermosetting resin and a preparation method thereof, in particular, a remoldable bismaleimide resin and preparation, remolding method, and relates to the technical field of polymer materials.

TECHNICAL BACKGROUND

Thermosetting resin is an important polymer material, accounting for about 18% of the total polymer. Thermosetting resins are widely used in many fields such as electronic information, energy, aerospace, transportation and so on as composite material matrix, coatings, adhesives, etc. With the increasing severity of environmental pollution and the continuous penetration of the concept of green sustainable development, the recycling and reuse of thermoset materials after their effective service life has become an urgent problem to be solved. At the same time, with the rapid development of electronic technology, the life cycle of a large number of electronic products and smart devices has been significantly shortened. For example, the use time of mobile phones is less than 18 months, and the use time of computers is less than 3 years. The total amount of discarded electronic products worldwide is as high as 20 to 50 million tons. Therefore, the recycling of thermosetting materials is particularly urgent. Due to the covalent cross-linking network, traditional thermosetting resins cannot be reprocessed or reshaped by heating or using solvents. Most thermosetting resins cannot be effectively recycled. The disposal methods of these waste thermosetting resins are usually: incineration, Landfill and degrade into small molecules by strong acid or alkali. The above-mentioned treatment methods have undoubtedly brought tremendous pressure to the increasingly severe energy shortage and environmental pollution problems. Therefore, the development of remoldable thermosetting resin is a problem that needs to be solved urgently.

The remoldable thermosetting resin developed by the prior art generally has the problem of low comprehensive performance (initial thermal decomposition temperature <350° C., glass transition temperature <180° C., tensile strength <80 MPa, tensile modulus <2700 MPa), which limits the application of remoldable thermosetting resins in high-performance fields.

In addition, multifunctionalization is the trend of research and development of today's materials. Shape memory polymers (SMPs) have broad application prospects in the fields of space self-expanding structures, shape deformation structures, intelligent jet propulsion systems, and high-temperature sensors and actuators. However, traditional thermoset SMPs cannot be reshaped, and the existing technologies developed remoldable thermoset SMPs are limited by the performance of the remoldable thermoset matrix, and also suffer from poor heat resistance and mechanical properties.

In summary, the development of a new type of thermosetting resin with high temperature resistance and high mechanical strength, reshaping and shape memory function is a subject of great application value.

THE INVENTION CONTENT

The purpose of the present invention is to provide a remoldable bismaleimide resin with high heat resistance, high tensile performance and good shape memory performance as well as its preparation and application method aiming at the shortcomings of existing technologies.

The present invention adopts the following technical scheme,

A remoldable bismaleimide resin, wherein the preparation method of remoldable bismaleimide resin comprising the following steps,
(1) In the presence of a quaternary ammonium salt, bis(3-(2-allylphenoxy)-2-hydroxypropyl) terephthalate is synthesized by reacting 2-allylphenyl glycidyl ether and terephthalic acid;
(2) Remoldable bismaleimide resin system is synthesized by reacting bis(3-(2-allylphenoxy)-2-hydroxypropyl) terephthalate, bismaleimide, and a zinc compound;
(3) The remoldable bismaleimide resin is prepared using cured and post-treated remoldable bismaleimide resin system.

A remolded bismaleimide resin. The preparation method of remolded bismaleimide resin includes the following steps, the remolded bismaleimide resin is prepared using the hot pressing treatment to heat the pulverizedremoldable bismaleimide resin.

A preparation method for remolding bismaleimide resin includes the following steps:
(1) In the presence of a quaternary ammonium salt, bis(3-(2-allylphenoxy)-2-hydroxypropyl) terephthalate is synthesized by reacting 2-allylphenyl glycidyl ether and terephthalic acid;
(2) Remoldable bismaleimide resin system is synthesized by reacting bis(3-(2-allylphenoxy)-2-hydroxypropyl) terephthalate, bismaleimide, and a zinc compound;
(3) The remoldable bismaleimide resin is prepared using cured and post-treated remoldable bismaleimide resin system;
(4) The remolded bismaleimide resin is prepared with remoldable bismaleimide resin being pulverized and hot pressing treated to realize the remolding of the bismaleimide resin.

In the present invention, the 2-allylphenyl glycidyl ether is synthesized by adding epichlorohydrin to a mixture of 2-allylphenol, sodium hydroxide, a quaternary ammonium salt, and tetrahydrofuran.

In the present invention, in the step (1), a mass ratio of 2-allylphenyl glycidyl ether, terephthalic acid and quaternary ammonium salt is 120:40-50:5-10, a reaction temperature is 65-80° C. and a reaction time is 8-12 h; in the step (2), a mass ratio of bismaleimide, bis(3-(2-allylphenoxy)-2-hydroxypropyl) terephthalate and the zinc compound is 50:65.5-114:6.76-11.76, a stirring temperature is 120-135° C., and a reaction time is 15-25 min; in the step (3), the remoldable bismaleimide resin system is cured and post-treated by casting; in the step (4), a temperature of hot pressing treatment is 240-300° C., a pressure is 20-40M Pa and a reaction time is 2-8 h.

In the present invention, the quaternary ammonium salt is tetramethylammonium bromide and/or tetrabutylammonium bromide; the zinc compound is zinc acetylacetonate hydrate; the bismaleimide is one or more selected from the group consisting of N,N'-4,4'-diphenylmethane bismaleimide, N,N'-(1,4-phenylene) bismaleimide and N,N'-m-phenylene bismaleimide.

The present invention also discloses the application of remoldable bismaleimide resin in the preparation of remoldable materials or remoldable thermosetting resins.

The present invention discloses a preparation method of the remoldable bismaleimide resin, which includes the following steps.

The solution A is obtained by 120 parts of 2-allylphenol, 100-150 parts of NaOH, 5-10 parts of quaternary ammonium salt and 200-300 parts of tetrahydrofuran were maintained and stirred at 25-40° C. for 1-2 h; 2-allylphenyl glycidyl ether is obtained: 250-350 parts of epichlorohydrin is slowly added into the solution A, which is maintained the temperature for 6-10 h.

Bis(3-(2-allylphenoxy)-2-hydroxypropyl) terephthalate is obtained: 120 parts of 2-allylphenyl glycidyl ether, 40-50 parts of terephthalic acid, 5-10 parts of quaternary ammonium salt and 200-300 parts of acetonitrile are maintained and stirred at 65-80° C. for 8-12 h.

Clear prepolymer (remoldable bismaleimide resin system) is obtained by 50 parts of bismaleimide, 65.5-114 parts of bis(3-(2-allylphenoxy)-2-hydroxypropyl) terephthalate and 6.76-11.76 parts of zinc acetylacetonate are stirred at 120-135° C. for 15-25 min. Then curing and post-treatment to obtain a remoldable bismaleimide resin.

The amount of the above raw materials is based on the mass. The curing and post-treatment can be specifically as follows, pouring the clarified prepolymer into a mold, putting it in a vacuum oven at 130° C. and vacuuming for 45 minutes; moving the vacuumed prepolymer into a blast drying box, and curing and post-curing according to the following process: 160° C./2 h+180° C./2 h+200° C./2 h+220° C./2 h and 240° C./4 h; demold after natural cooling, and get remoldable bismaleimide resin.

BENEFICIAL EFFECT

Compared with existing technologies, the beneficial effects of the present invention are as follows, 1. The invention synthesizes a novel bisallyl compound containing a reversible dynamic group, uses it to modify the bismaleimide, and prepares a novel remoldable bismaleimide resin containing a reversible covalent bond.

2. Compared with the remoldable thermosetting resin reported in the existing literature, the remoldable bismaleimide resin prepared by the present invention has outstanding heat resistance, which is characterized by an initial thermal decomposition temperature ($T_{di}$) of 375° C., glass The transformation temperature (Tg) reaches 203° C. Unlike remoldable thermosetting resins based on disulfide bonds, schiff bases, vinylogous urethane and other reversible covalent bonds, the reversible covalent bonds selected in the present invention have better heat resistance, so the prepared resin has higher thermal stability In addition, the good performance of the resin also benefits from the reasonable formula of the resin system, the preparation process, and the large number of benzene rings in the resin and the six-membered ring formed by curing.

3. Compared with the remoldable thermosetting resins reported in the existing literature, the remoldable bismaleimide resin prepared by the present invention has outstanding tensile properties, with a tensile strength of 84 MPa and a tensile modulus of 3233 MPa. The remoldable bismaleimide resin has good tensile properties due to the large number of benzene rings in the resin and the six-membered ring formed by curing.

4. Compared with the remoldable thermosetting resin reported in the existing literature, the remoldable bismaleimide resin prepared by the present invention has a good shape memory function, because the synthesized new bisallyl compound bis(3-(2-allylphenoxy)-2-hydroxypropyl) terephthalate has good rotational flexibility; in addition, the crosslink density of the cured resin is moderate, which is beneficial to obtain good shape memory performance.

5. Compared with the traditional 2,2'-diallyl bisphenol A, the new diallyl compound provided by the present invention-bis(3-(2-allylphenoxy)-2-hydroxypropyl) The synthesis of terephthalate does not require high-temperature rearrangement, the synthesis process is simple, and the required energy consumption is small.

6. Compared with the traditional 2,2'-diallyl bisphenol A, the bis(3-(2-allylphenoxy)-2-hydroxypropyl) terephthalate synthesized in the present invention is Non-bisphenol A type, therefore, there is no risk of carcinogenesis, teratogenicity, and fertility effects of BPA.

EXAMPLES

The technical scheme of the present invention is further elaborated in combination with attached Figures and Examples.

A remoldable bismaleimide resin. The preparation method of remoldable bismaleimide resin includes the following steps.

(1) In the presence of a quaternary ammonium salt, bis(3-(2-allylphenoxy)-2-hydroxypropyl) terephthalate is synthesized by reacting 2-allylphenyl glycidyl ether and terephthalic acid;
(2) A remoldable bismaleimide resin system is synthesized by mixing bis(3-(2-allylphenoxy)-2-hydroxypropyl) terephthalate, bismaleimide, and a zinc compound;
(3) A remoldable bismaleimide resin is prepared by curing and post-treating a remoldable bismaleimide resin system.

Example 1

Figure 1:
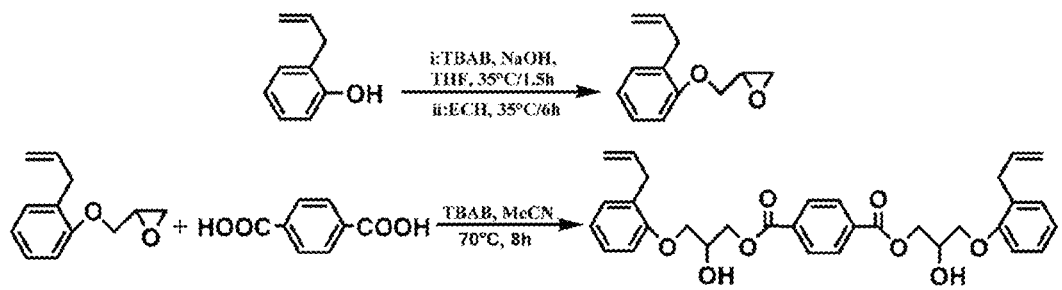
FIG. 1 shows a synthesis reaction formula of 2-allylphenyl glycidyl ether and bis(3-(2-allylphenoxy)-2-hydroxypropyl) terephthalate prepared in the present invention.
Figure 2:
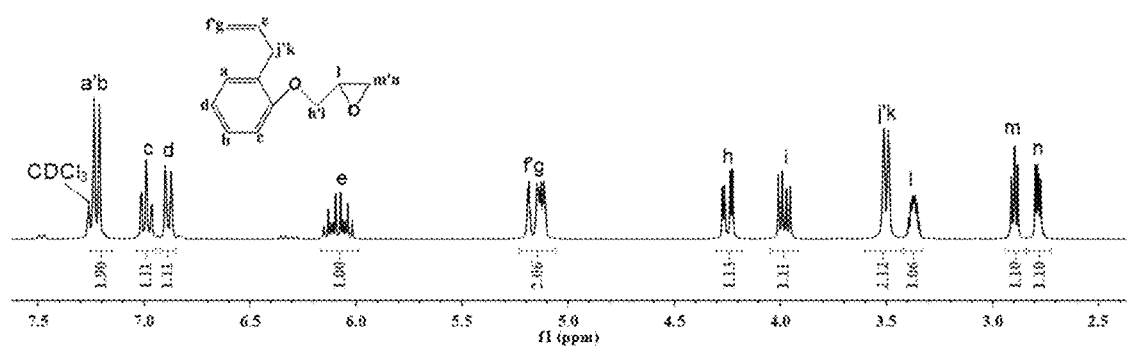
FIG. 2 shows $^1$HNMR spectra of 2-allylphenyl glycidyl ether prepared in Example 1.

1) The preparation of 2-allylphenyl glycidyl ether. By mass, the solution A was obtained: 120 g of 2-allylphenol, 140 g of NaOH, 10 g of tetrabutylammonium bromide and 230 g of tetrahydrofuran were maintained and stirred at 35° C. for 1.5 h; and then, 270 g of epichlorohydrin was slowly added into the solution A, which was maintained at 35° C. for 6 h. After the reaction, tetrahydrofuran and epichlorohydrin were removed in vacuum rotary evaporation propane to give a crude product. The crude product was washed with saturated $NH_4Cl$ solution (200 ml×2) and deionized water (200 mL×2) successively. Finally separating and purifying by using column chromatography to obtain a yellow viscous liquid which is 2-allylphenyl glycidyl ether (yield was 93%), the reaction formula and $^1$H-NMR are shown in FIGS. 1 and 2, respectively.

2) The preparation of bis(3-(2-allylphenoxy)-2-hydroxypropyl) terephthalate. By mass, 120 g of 2-allylphenyl glycidyl ether, 45 g of terephthalic acid, 10 g of tetrabutylammonium bromide and 230 g of acetonitrile were maintained and stirred at 70° C. for 8 h. After the reaction, acetonitrile was removed in vacuum rotary evaporation propane to give a crude product. The crude product was washed with saturated $NaHCO_3$ solution (200 ml×2) and deionized water (200 mL×2) successively. Finally separating and purifying by using column chromatography to obtain a yellow oil product which is bis(3-(2-allylphenoxy)-2-hydroxypropyl) terephthalate (yield was 86%), the reaction formula, $^1$HNMR, $^{13}$CNMR and high resolution mass spectrum are shown in FIGS. 1, 3, 4 and 5, respectively.

3) The preparation of remoldable bismaleimide resin, N,N'-4,4'-diphenylmethane bismaleimide 50 g (139.5 mmol), bis(3-(2-allylphenoxy)-2-hydroxypropyl) terephthalate 76.17 g (139.5 mmol) and zinc acetylacetonate hydrate 7.86 g (27.9 mmol) and stirred and prepolymerized at 120° C. for 20 min to obtain a clear prepolymer; poured the clarified prepolymer into the preheated mold at 130° C., put it in a vacuum oven at 130° C. and vacuuming for 45 minutes; moved the evacuated prepolymer into a blast drying oven, and solidify according to the following process post-treatment: 160° C./2 h+180° C./2 h+200° C./2 h+220° C./2 h and 240° C./4 h; after natural cooling, demolding, the remoldable bismaleimide resin can be obtained. The DSC curves of the clarified prepolymer of the remoldable bismaleimide resin, the TGA curves, the Tan δ-temperature curves, tensile stress-strain curves, the consecutive dual-shape memory cycles, stress relaxation curves of the remoldable bismaleimide resin are shown in FIGS. 6, 7, 8, 9, 10, and 11 respectively.

Figure 12:
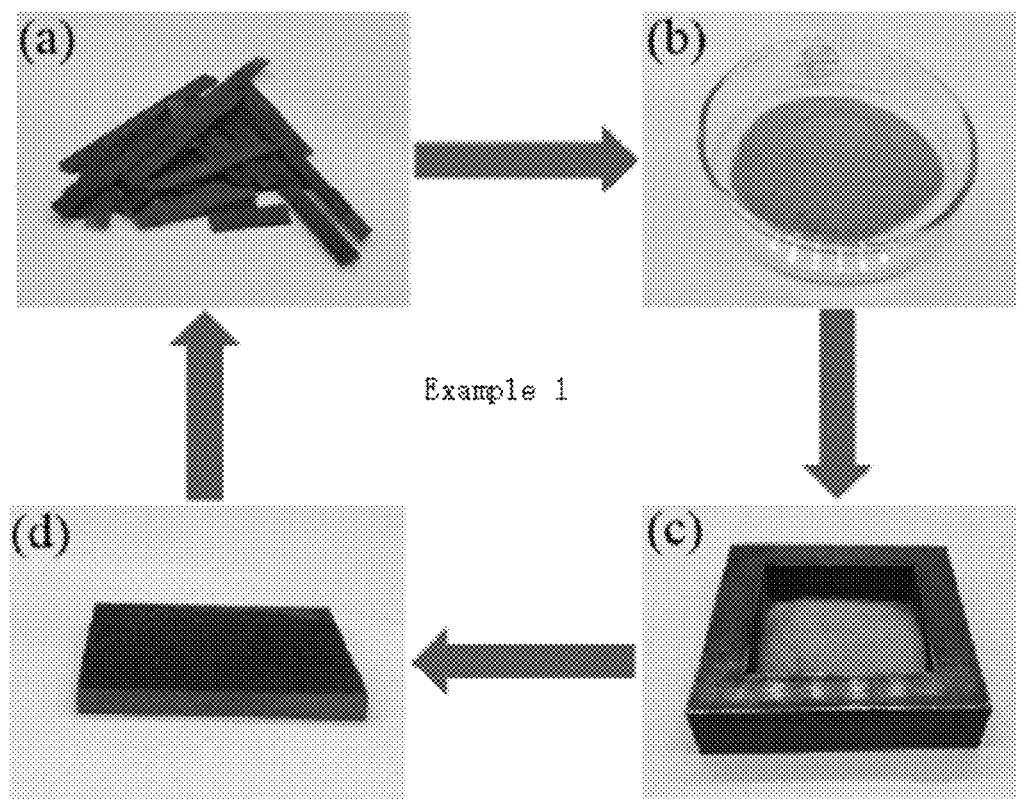
FIG. 12 shows digital photographs during the remolding process of the remoldable bismaleimide resins prepared in Example 1, a, b, c, d represent the state of each stage.
Figure 13:
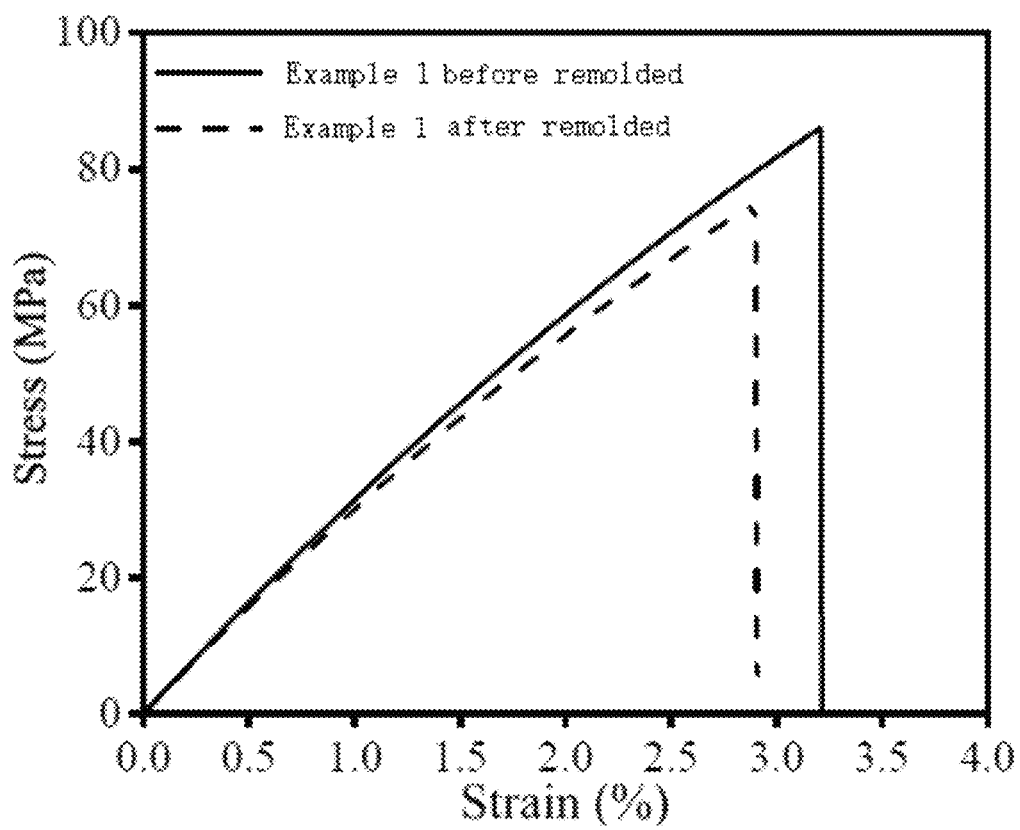
FIG. 13 shows tensile stress-strain curves of the remoldable bismaleimide resin prepared in Example 1 before and after remolding
Figure 14:
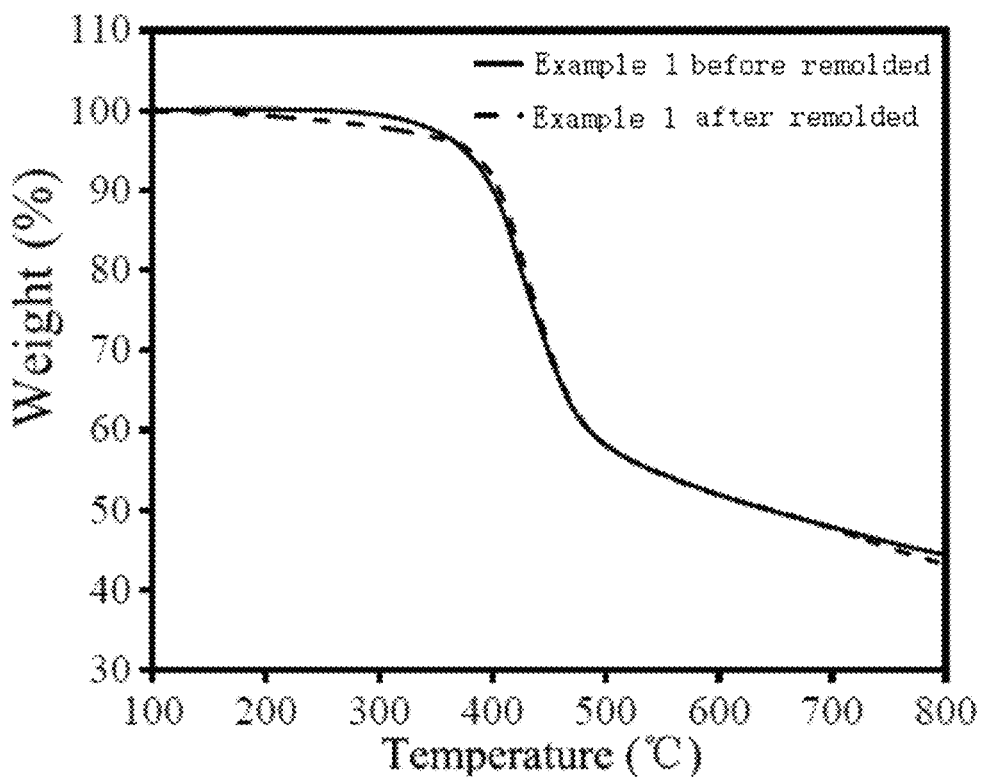
FIG. 14 shows TGA curves of the remoldable bismaleimide resin prepared in Example 1 before and after remolding.

4) Remolding method of remoldable bismaleimide resin and remolded bismaleimide resin, pressing down the pulverized remoldable bismaleimide resin at 270° C. and 30 MPa for 4 h; After natural cooling released the mold to obtain the remoldable bismaleimide resin, which realized the remolding of the bismaleimide resin. The surface of the obtained remolded resin block is smooth without cracks, indicating that the resin particles have undergone a dynamic transesterification reaction to reconnect the particles. This result fully proves that the bismaleimide resin can be reshaped by the present invention. The digital photographs during the remolding process of the remoldable bismaleimide resins, the tensile stress-strain curves and the TGA curves of the remoldable bismaleimide resins are shown in FIGS. 12, 13, and 14, respectively.

Refer to FIGS. 2, it shows $^1$HNMR spectra of 2-allylphenyl glycidyl ether prepared in Example 1. In this figure, there are proton resonances on allyl and benzene rings, and characteristic peaks of epoxy group protons appear near 2.80 ppm, 2.90 ppm and 3.36 ppm, indicating that 2-allylphenol has reacted with epichlorohydrin and 2-allylphenyl glycidyl ether was produced.

Figure 3:
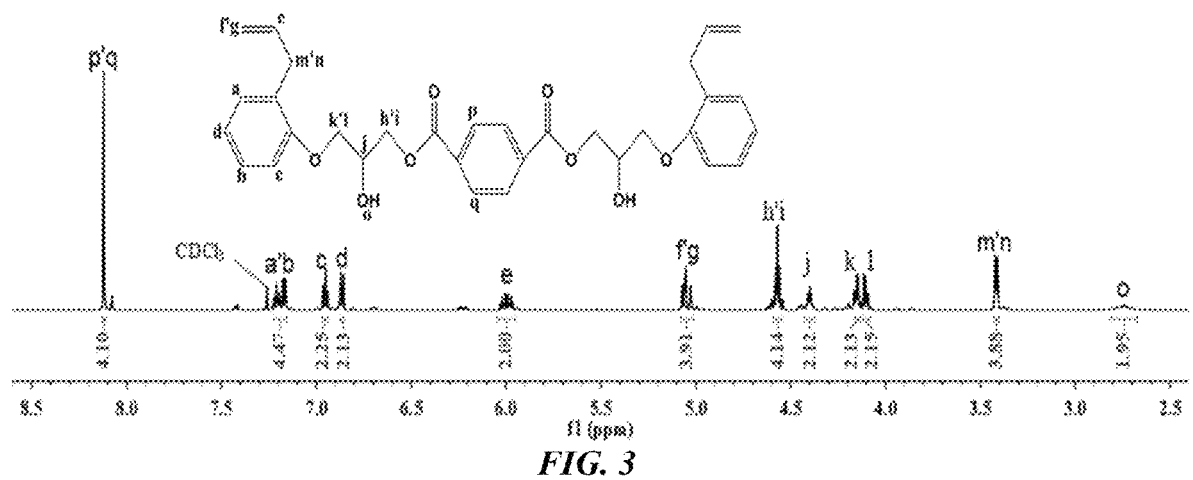
FIG. 3 shows $^1$HNMR spectra of bis(3-(2-allylphenoxy)-2-hydroxypropyl) terephthalate prepared in Example 1.

Refer to FIG. 3, it shows $^1$HNMR spectra of bis(3-(2-allylphenoxy)-2-hydroxypropyl) terephthalate prepared in Example 1. In this figure, there are proton resonances on the allyl and benzene rings. Although the characteristic peak of the proton of the epoxy group has disappeared, the characteristic peak of the proton of —OH appears near 2.74 ppm, indicating that the epoxy group has reacted with the carboxyl group and generated β-hydroxy ester.

Figure 4:
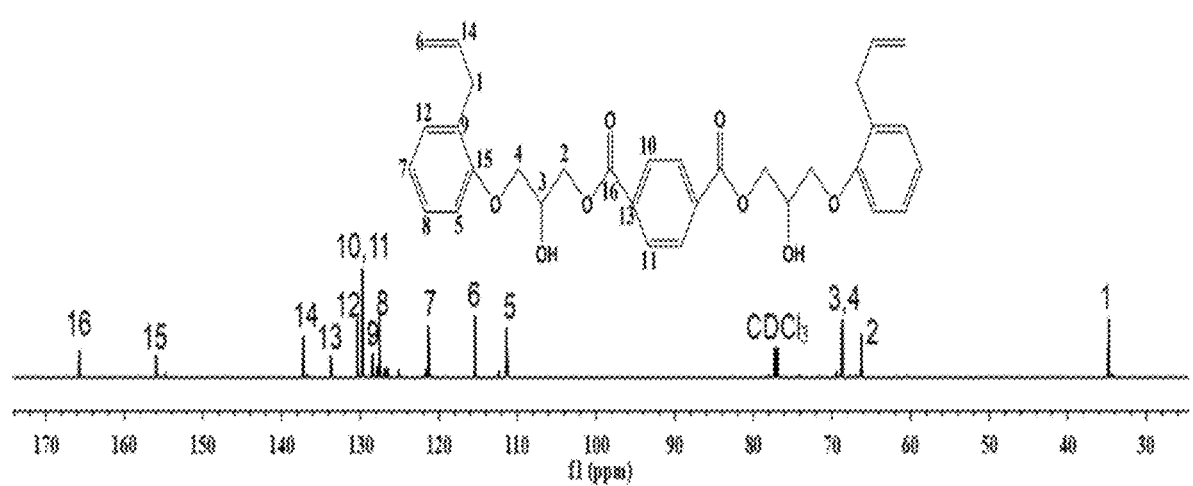
FIG. 4 shows $^{13}$CNMR of bis(3-(2-allylphenoxy)-2-hydroxypropyl) terephthalate prepared in Example 1.

Refer to FIG. 4, it shows $^{13}$CNMR of bis(3-(2-allylphenoxy)-2-hydroxypropyl) terephthalate prepared in Example 1. The number and position of C shown in this figure correspond to bis(3-(2-allylphenoxy)-2-hydroxypropyl) terephthalate.

Figure 5:
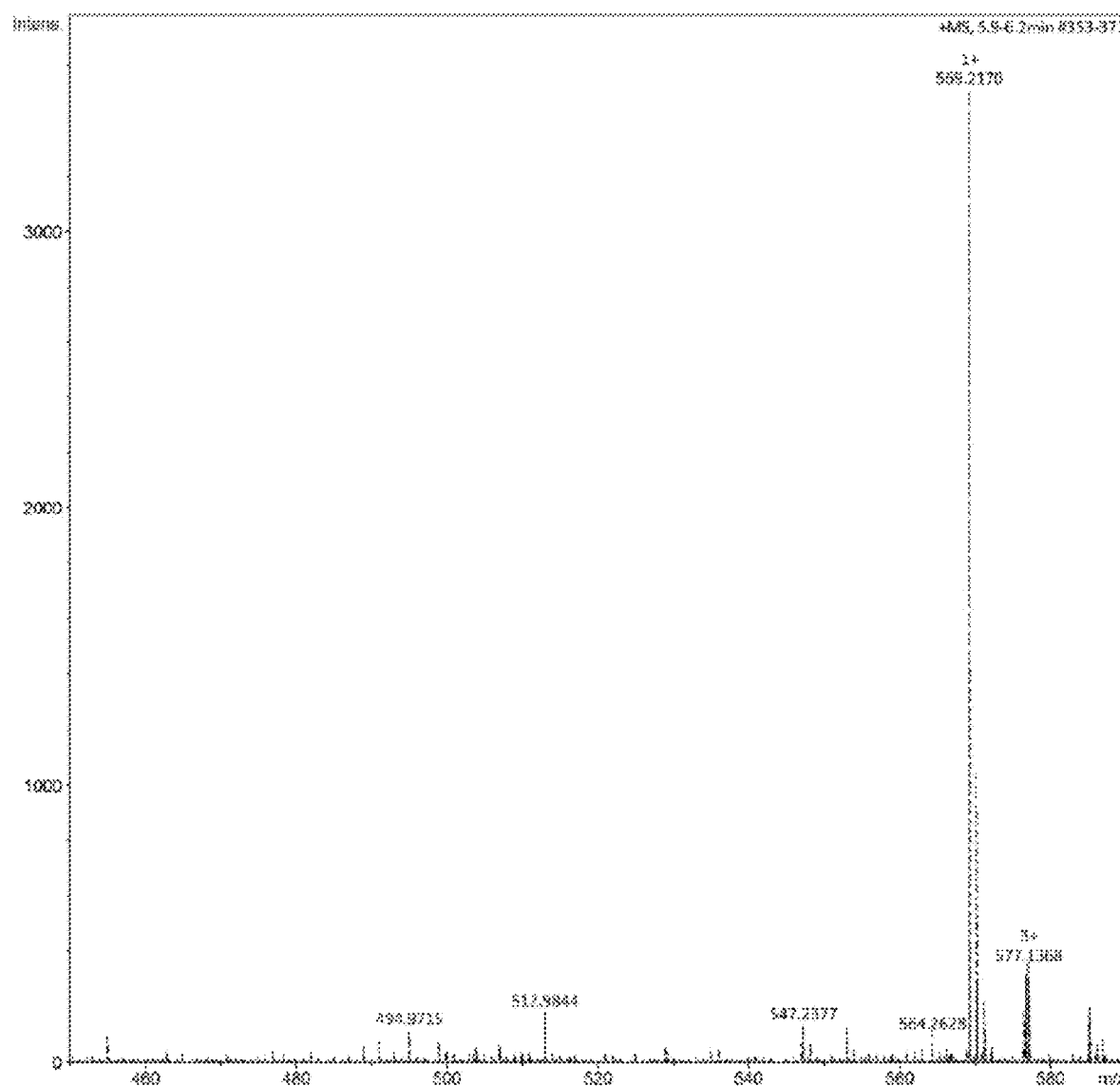
FIG. 5 shows high resolution mass spectrum of bis(3-(2-allylphenoxy)-2-hydroxypropyl) terephthalate prepared in Example 1.

Refer to FIG. 5, it shows high resolution mass spectrum of bis(3-(2-allylphenoxy)-2-hydroxypropyl) terephthalate prepared in Example 1. The theoretical molecular weight [M] of bis(3-(2-allylphenoxy)-2-hydroxypropyl) terephthalate is 546.2254, and the theoretical value [M+Na$^+$] is 569.2146, is in agreement with experimental value is 569.2170.

Based on the above figures, it can be seen that Example 1 successfully synthesized bis(3-(2-allylphenoxy)-2-hydroxypropyl) terephthalate.

Control Example 1

Figure 9:
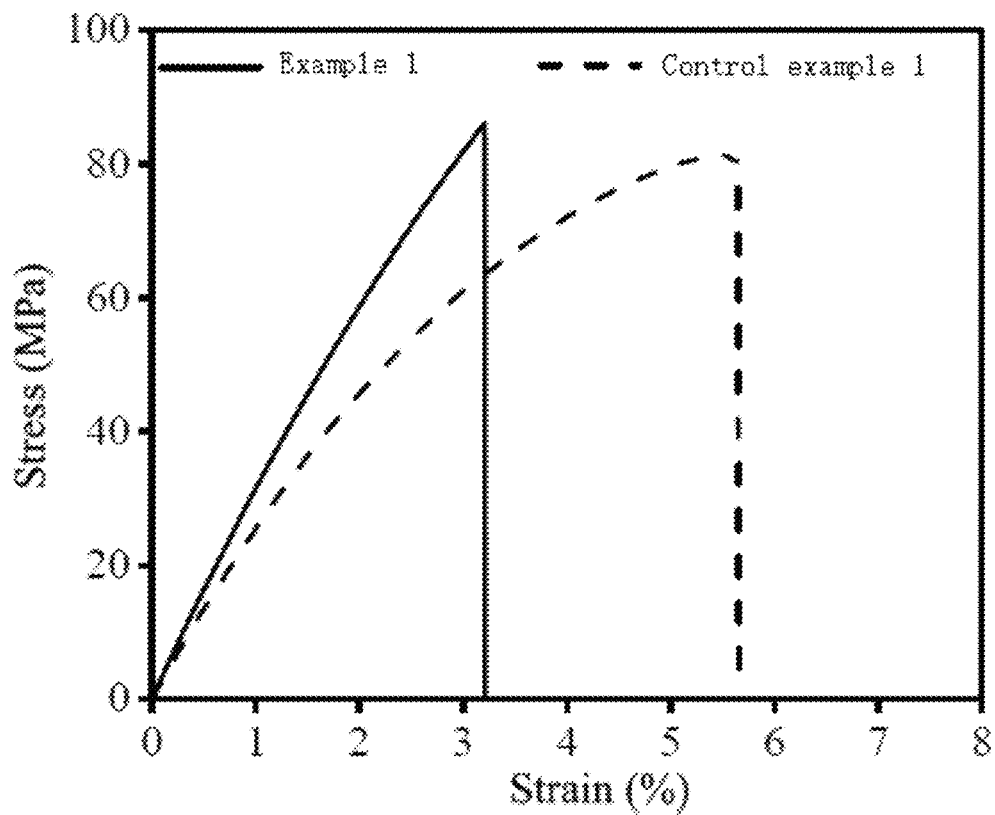
FIG. 9 shows tensile stress-strain curves of the remoldable bismaleimide resin prepared in Example 1 and the diallyl bisphenol A modified bismaleimide resin of Control Example 1.

1) Preparation of diallyl bisphenol A modified bismaleimide resin, N,N'-4,4'-diphenylmethane bismaleimide 50 g (139.5 mmol), 2,2'-diallyl bisphenol A 43.03 g (139.5 mmol) and zinc acetylacetonate hydrate 7.86 g (27.9 mmol) and stirred and prepolymerized at 120° C. for 20 min to obtain a clear prepolymer; poured the clarified prepolymer into the preheated mold at 130° C., put it in a vacuum oven at 130° C. and vacuuming for 45 minutes; moved the evacuated prepolymer into a blast drying oven, and solidify according to the following process post-treatment: 160° C./2 h+180° C./2 h+200° C./2 h+220° C./2 h and 240° C./4 h; after natural cooling, demolding, the diallyl bisphenol A modified bismaleimide resin can be obtained. The DSC curves of the clarified prepolymer of the diallyl bisphenol A modified bismaleimide resin, the tensile stress-strain curves of the diallyl bisphenol A modified bismaleimide resin are shown in FIGS. 6 and 9 respectively.

2) Remoldability of the diallyl bisphenol A modified bismaleimide resin, pressing down the pulverized the diallyl bisphenol A modified bismaleimide resin at 270° C. and 30 MPa for 4 h; the obvious granular plate was obtained after natural cooling and released the mold. The surface of the board has obvious graininess, is easy to break, and has almost no mechanical strength, which proves that the diallyl bisphenol A modified bismaleimide resin cannot be reshaped. The digital photographs during the remolding process of the diallyl bisphenol A modified bismaleimide resin prepared in Control Example 1 refer to FIG. 15.

Figure 6:
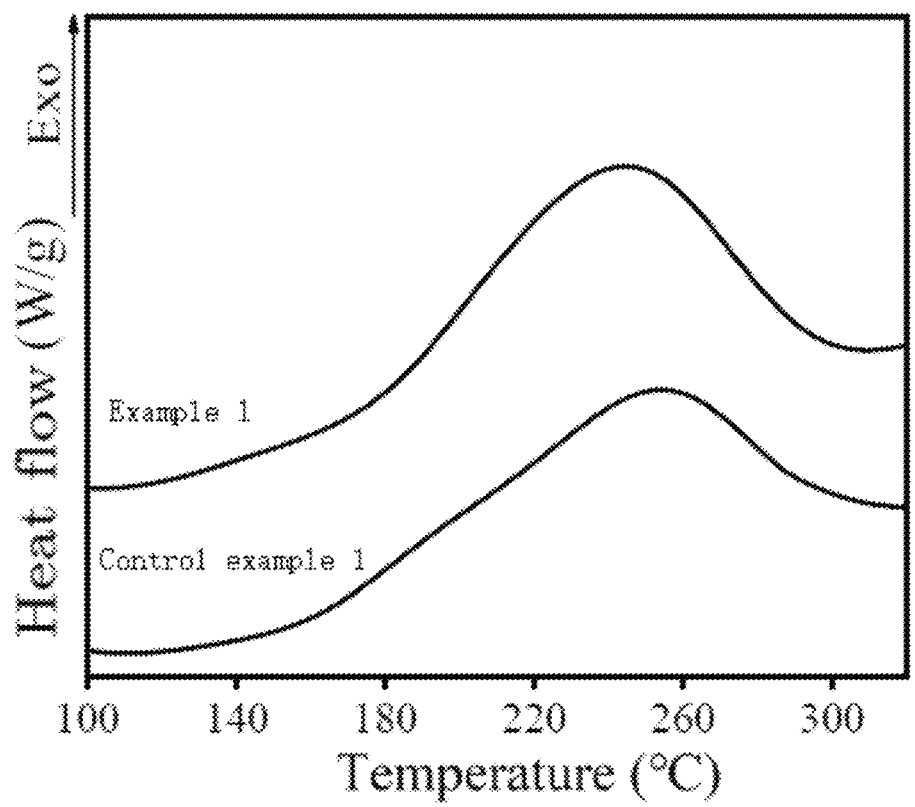
FIG. 6 shows the DSC curves of the prepolymer of the remoldable bismaleimide resin prepared in Example 1 and the diallyl bisphenol A modified bismaleimide resin of Control Example 1 under nitrogen atmosphere, the heating rate is 10° C./min.

Refer to FIG. 6, it shows the DSC curves of the prepolymer of the remoldable bismaleimide resin prepared in Example 1 and the diallyl bisphenol A modified bismaleimide resin of Control Example 1 under nitrogen atmosphere, the heating rate is 10° C./min. It can be seen that the maximum reaction exothermic peak of the remoldable bismaleimide resin of Example 1 is at 245.7° C., which is lower than that at 254.5° C. of the diallyl bisphenol A modified bismaleimide resin in Control Example 1, it indicates that the reactivity of the remoldable bismaleimide resin of Example 1 is greater than that of the diallyl bisphenol A modified bismaleimide resin in Control Example 1.

Figure 7:
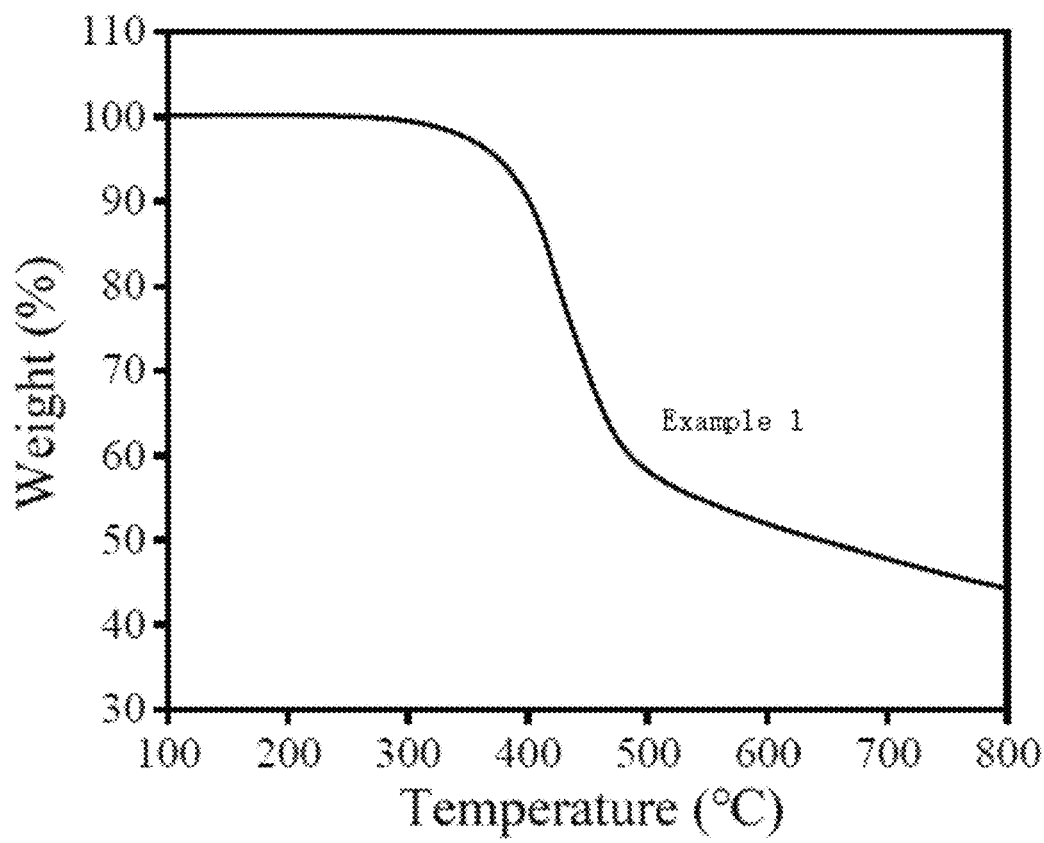
FIG. 7 shows TGA curves of the remoldable bismaleimide resin prepared in Example 1 under a nitrogen atmosphere, and the heating rate is 10° C./min.

Refer to FIG. 7, it shows TGA curves of the remoldable bismaleimide resin prepared in Example 1 under a nitrogen atmosphere. In general, the thermal stability of a material is characterized by the initial thermal decomposition temperature. The $T_{di}$ is higher the better, so the remoldable bismaleimide resin has good heat resistance, and its $T_{di}$ is 375° C. The existing literature reports that the $T_{di}$ of the remoldable thermosetting resin is generally lower than 350° C. (see Table 1).

Refer to attached table 1, which is the $T_{di}$, T g, tensile strength and tensile modulus of the remoldable bismaleimide resin prepared in Example 1 of the present invention and the high-performance remoldable thermosetting resin reported in the existing literature and other performance parameters. The documents listed in Table 1 are representative of remoldable thermosetting resins with good heat resistance or tensile properties in the prior art. It can be seen that, compared with the remoldable thermosetting resin reported in the existing literature, the remoldable bismaleimide resin prepared in Example 1 of the present invention has good heat resistance and tensile properties.

TABLE 1 heat resistance or tensile properties of remoldable thermosetting resins in the prior art

| High performance remouldable thermosetting resin | $T_{di}$ (° C.) | $T_g$ (° C.) | tensile strength (MPa) | tensile modulus (MPa) | reference |
|---|---|---|---|---|---|
| Example 1 | 375 | 203 | 84 | 3233 | this patent |
| Epoxy/bismaleimide ester exchange system | 366 | 125 | / | / | [1] |
| Epoxy ester exchange system | 365 | 82 | 54 | 2250 | [2] |
| Epoxy ester exchange system | 302 | 187 | 69.2 | 1950 | [3] |
| Epoxy disulfide bond system | ~350 | 80 | 14 | / | [4] |
| Epoxy Schiff base system | 300 | 103 | 88 | / | [5] |
| Epoxy Schiff base system | 303 | 87 | 85 | / | [6] |
| Epoxy Schiff base system | 323 | 172 | 81 | 2112 | [7] |
| Epoxy Schiff base system | 298.4 | 100 | 72.77 | 2682.5 | [8] |
| Epoxy spiro dental system | 278 | 169 | 85 | 3131 | [9] |
| Vinylogous Urethane system | 310 | 87 | 92 | 2100 | [10] |
| Polyimide Schiff base system | 289 | 218 | 80.6 | 1360 | [11] |

REFERENCES

[1] Ding, Z.; Yuan, L.; Guan, Q.; Gu, A.; Liang, G., A reconfiguring and self-healing thermoset epoxy/chain-extended bismaleimide resin system with thermally dynamic covalent bonds. *Polymer* 2018, 147, 170-182.

[2] Han, J.; Liu, T.; Hao, C.; Zhang, S.; Guo, B.; Zhang, J., A Catalyst-Free Epoxy Vitrimer System Based on Multifunctional Hyperbranched Polymer. *Macromolecules* 2018, 51 (17), 6789-6799.

[3] Liu, T.; Hao, C.; Zhang, S.; Yang, X.; Wang, L.; Han, J.; Li, Y.; Xin, J.; Zhang, J., A Self-Healable High Glass Transition Temperature Bioepoxy Material Based on Vitrimer Chemistry. *Macromolecules* 2018, 51 (15), 5577-5585.

[4] Chen, Q.; Yu, X.; Pei, Z.; Yang, Y.; Wei, Y.; Ji, Y., Multi-stimuli responsive and multi-functional oligoaniline-modified vitrimers. *Chem Sci* 2017, 8 (1), 724-733.

[5] Ruiz de Luzuriaga, A.; Martin, R.; Markaide, N.; Rekondo, A.; Cabanero, G.; Rodriguez, J.; Odriozola, I., Epoxy resin with exchangeable disulfide crosslinks to obtain reprocessable, repairable and recyclable fiber-reinforced thermoset composites. *Materials Horizons* 2016, 3 (3), 241-247.

[6] Mai, V. D.; Shin, S. R.; Lee, D. S.; Kang, I., Thermal Healing, Reshaping and Ecofriendly Recycling of Epoxy Resin Crosslinked with Schiff Base of Vanillin and Hexane-1,6-Diamine. *Polymers (Basel)* 2019, 11 (2), 293.

[7] Wang, S.; Ma, S.; Li, Q.; Xu, X.; Wang, B.; Yuan, W.; Zhou, S.; You, S.; Zhu, J., Facile in situ preparation of high-performance epoxy vitrimer from renewable resources and its application in nondestructive recyclable carbon fiber composite. *Green Chemistry* 2019, 21, 1484-1497.

[8] Liu, H.; Zhang, H.; Wang, H.; Huang, X.; Huang, G.; Wu, J., Weldable, malleable and programmable epoxy vitrimers with high mechanical properties and water insensitivity. *Chemical Engineering Journal* 2019, 368, 61-70.

[9] Ma, S.; Wei, J.; Jia, Z.; Yu, T.; Yuan, W.; Li, Q.; Wang, S.; You, S.; Liu, R.; Zhu, J., Readily recyclable, high-performance thermosetting materials based on a lignin-derived spiro diacetal trigger. *Journal of Materials Chemistry A* 2019, 7 (3), 1233-1243.

[10] Denissen, W.; Rivero, G.; Nicolay, R.; Leibler, L.; Winne, J. M.; Du Prez, F. E., Vinylogous Urethane Vitrimers. *Advanced Functional Materials* 2015, 25 (16), 2451-2457.

[11] Lei, X.; Jin, Y.; Sun, H.; Zhang, W., Rehealable imide-imine hybrid polymers with full recyclability. *J. Mater. Chem. A* 2017, 5 (40), 21140-21145.

Figure 8:
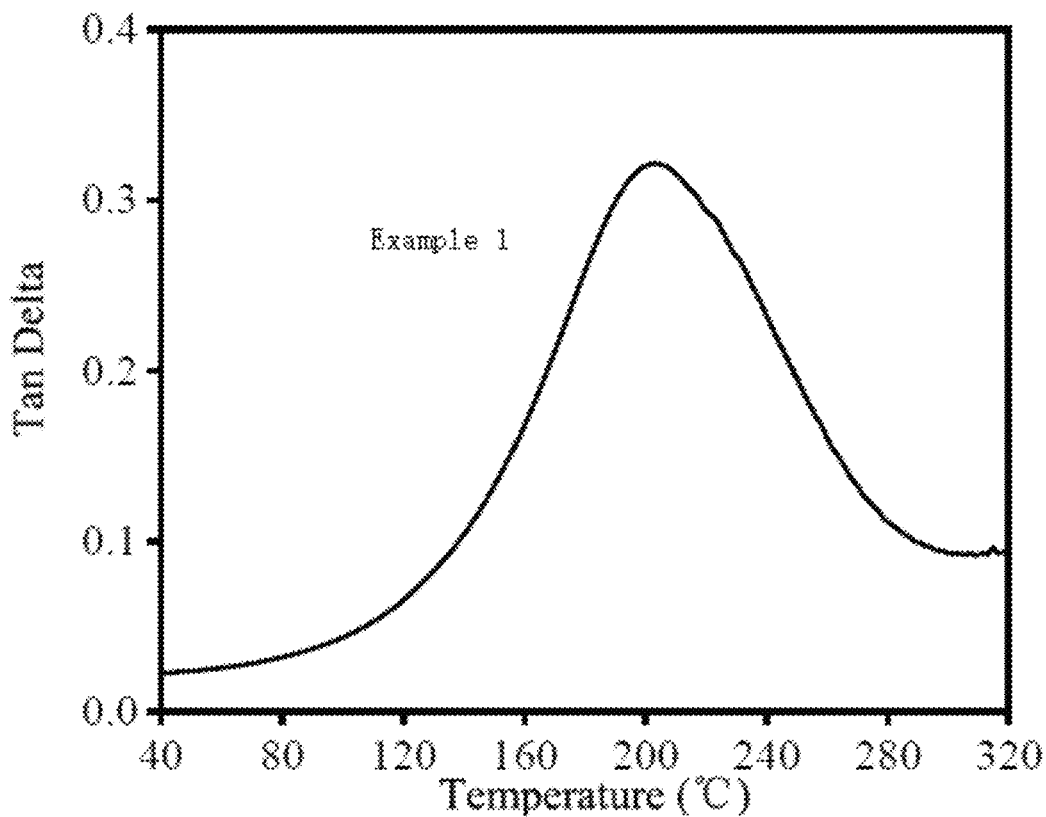
FIG. 8 shows Tan δ-temperature curves of the remoldable bismaleimide resin prepared in Example 1, the heating rate is 3° C./min, and the frequency is 1 Hz.

Refer to FIG. 8, it shows Tan δ-temperature curves of the remoldable bismaleimide resin prepared in Example 1. The curve presents a single symmetrical Tan δ peak, and the peak temperature of Tan δ serves as the glass transition temperature (Tg). Generally speaking, Tg represents the upper limit temperature of thermosetting materials. The Tg is higher the better. So the Tg of the remoldable bismaleimide resin is 203° C., showing good heat resistance. The existing literature currently reports that the Tg of the remoldable thermosetting resin is generally lower than 180° C. (see Table 1).

Refer to FIG. 9, it shows tensile stress-strain curves of the remoldable bismaleimide resin prepared in Example 1 and the diallyl bisphenol A modified bismaleimide resin of Control Example 1. It can be seen that the tensile strength of the remoldable bismaleimide resin prepared in Example 1 is 84 MPa, the tensile modulus is 3233 MPa, and the elongation at break is 3.16% (the existing literature reports that the remoldable thermosetting resin the tensile modulus is generally lower than 2700 MPa, see attached table 1); the diallyl bisphenol A modified bismaleimide resin prepared in Control Example 1 has a tensile strength of 81 MPa and a tensile modulus of 2595 MPa. The elongation at break is 5.62%.

Figure 10:
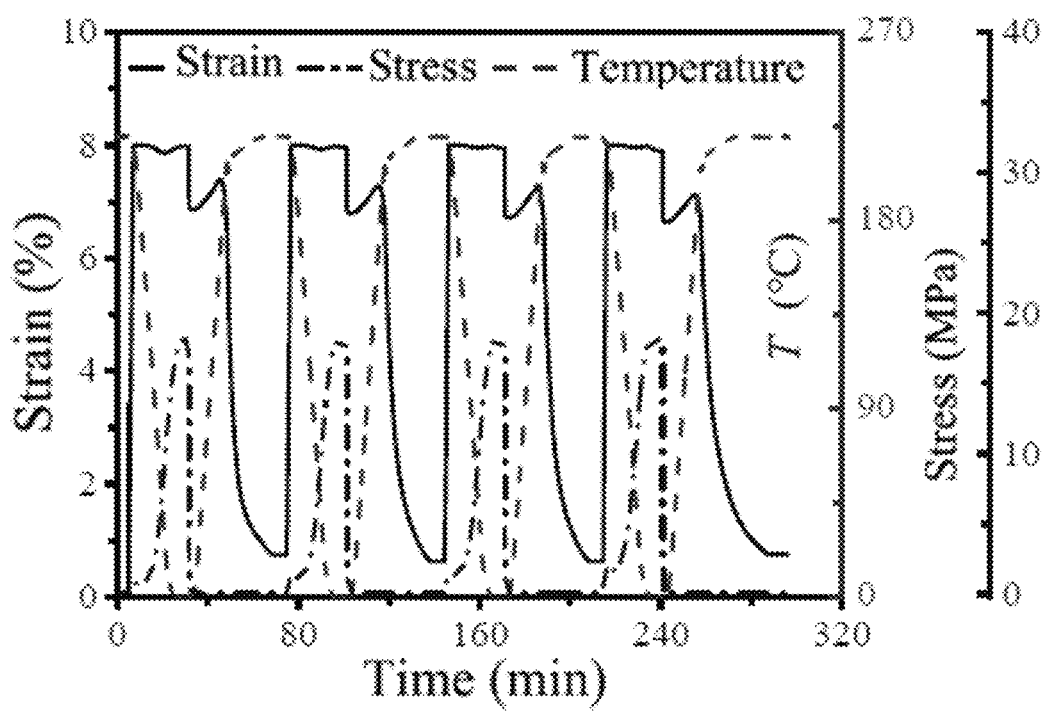
FIG. 10 shows consecutive dual-shape memory cycles of the remoldable bismaleimide resin prepared in Example 1.

Refer to FIG. 10, it shows consecutive dual-shape memory cycles of the remoldable bismaleimide resin prepared in Example 1. Generally speaking, shape fixation rate and shape recovery rate are important parameters to characterize the shape memory performance of materials. It can be seen that the shape fixation rate of the remoldable bismaleimide resin prepared in Example 1 is 86%, and the shape recovery rate is 92%. Both parameters have reached the mainstream level in the literature report. At the same time, in the present invention, the remoldable bismaleimide resin prepared in Example 1 also has higher heat resistance and tensile properties than the remoldable thermoset shape memory material reported in the prior literature, indicating that the remoldable bismaleimide resin prepared in Example 1 of the present invention combines good heat resistance, tensile properties and shape memory properties. In addition, after four cycles of testing, there is almost no change in the shape fixation rate and shape recovery rate of the resin, indicating that the remoldable bismaleimide resin prepared in Example 1 of the present invention has good shape memory cycle stability and performance shape fixation and shape recovery occurred multiple times.

Refer to FIG. 10, it shows consecutive dual-shape memory cycles of the remoldable bismaleimide resin prepared in Example 1. Generally speaking, shape fixation rate and shape recovery rate are important parameters to characterize the shape memory performance of materials. It can be seen that the shape fixation rate of the remoldable bismaleimide resin prepared in Example 1 is 86%, and the shape recovery rate is 92%. Both parameters have reached the mainstream level in the literature report. At the same time, in the present invention, the remoldable bismaleimide resin prepared in Example 1 also has higher heat resistance and tensile properties than the remoldable thermoset shape memory material reported in the prior literature, indicating that the remoldable bismaleimide resin prepared in Example 1 of the present invention combines good heat resistance, tensile properties and shape memory properties. In addition, after four cycles of testing, there is almost no change in the shape fixation rate and shape recovery rate of the resin, indicating that the remoldable bismaleimide resin prepared in Example 1 of the present invention has good shape memory cycle stability and performance shape fixation and shape recovery occurred multiple times.

Figure 11:
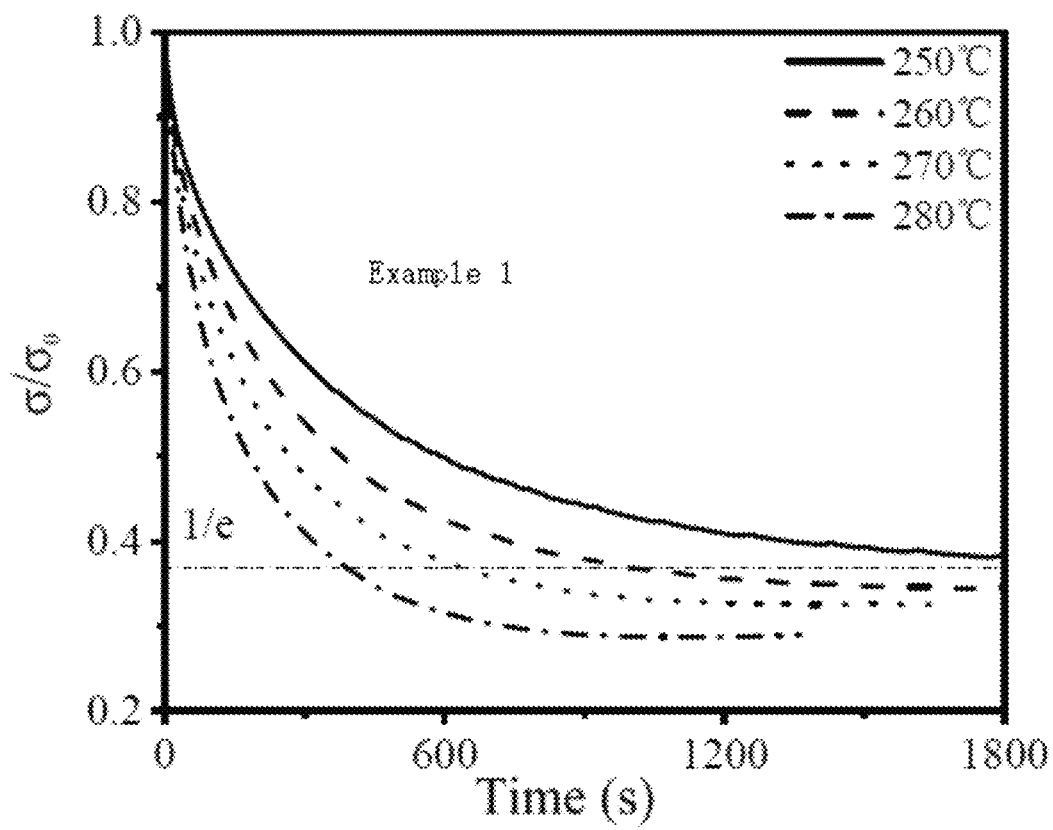
FIG. 11 shows stress relaxation curves of the remoldable bismaleimide resin prepared in Example 1 at different temperatures.

Refer to FIG. 11, shows stress relaxation curves of the remoldable bismaleimide resin prepared in Example 1 at different temperatures. It can be seen that as the temperature increases, the decay rate of the internal stress of the polymer becomes faster and faster. It can be seen from the trend that when the temperature reaches a certain value, the internal stress of the resin will attenuate to zero, which is similar to the stress relaxation curve of the thermoplastic resin, which proves that the reshape under heating remoldable bismaleimide resin can be like a thermoplastic resin.

Refer to FIG. 12, shows digital photographs during the remolding process of the remoldable bismaleimide resins prepared in Example 1, and the arrows indicate the process steps. The resin is pulverized into particles with a pulverizer; the resin particles are placed in a mold and molded at 270° C. and 30 MPa for 4 hours; the mold is released after natural cooling to obtain a remoldable bismaleimide board. The surface of the remolded resin is smooth, without cracks, and without graininess, indicating that the resin particles have been reconnected through the exchange of dynamic bonds, which proves that the bismaleimide resin prepared by the present invention can be remolded.

Refer to FIG. 13, is shows tensile stress-strain curves of the remoldable bismaleimide resin prepared in Example 1 before and after remolding. From this, we can intuitively compare the tensile properties of the resin before and after remolding. After remolding, the tensile strength of the resin is 72 MPa, the tensile modulus is 3071 MPa, the elongation at break is 2.92%, and the three parameters are repaired. The efficiencies were 86%, 95% and 92%, respectively, indicating that the reshaped bismaleimide resin still maintains good tensile properties.

Refer to FIG. 14, it shows TGA curves of the remoldable bismaleimide resin prepared in Example 1 before and after remolding. It can be seen that the TGA curves of the resin before and after remolding almost overlap, and the Tdi of the resin after remolding is at 378° C. It can be seen that the bonding strength of the chemical bond of the remolded resin is the same as that before the remolding, so that the remolded resin still has outstanding thermal stability.

In summary, the remoldable bismaleimide resin prepared by the present invention has outstanding heat resistance, high mechanical properties, good shape memory performance and good remolding performance.

Figure 15:
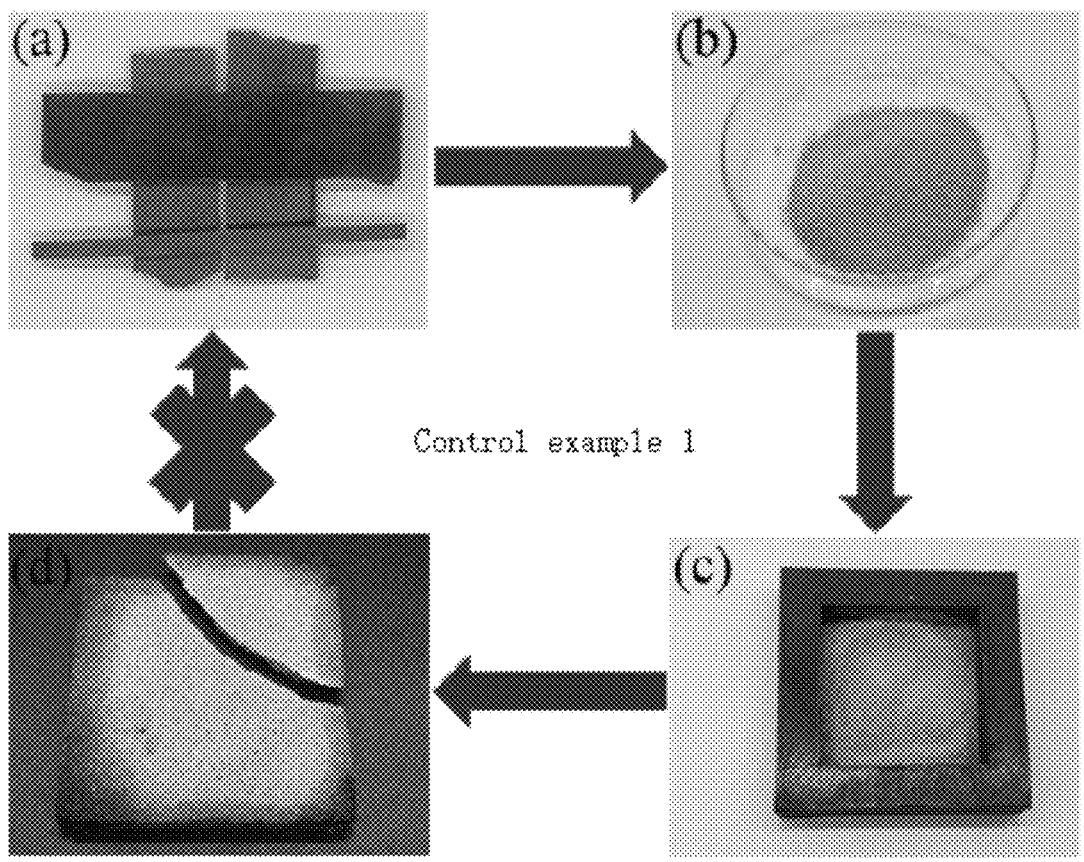
FIG. 15 shows digital photographs during the remolding process of the diallyl bisphenol A modified bismaleimide resin prepared in Control Example 1, a, b, c, d represent the state of each stage.

Refer to FIG. 15, it shows digital photographs during the remolding process of the diallyl bisphenol A modified bismaleimide resin prepared in Control Example 1, and the arrows indicate the process steps. The resin is pulverized into particles with a pulverizer; the resin particles are placed in a mold, and the resin particles are molded at 270° C. and 30 MPa for 4 hours; the mold is released after natural cooling to obtain a granular plate. The surface of the board has obvious graininess and is easy to break. It has almost no mechanical strength, indicating that the resin particles are only close to each other under the action of external pressure, and they are not reconnected to each other. The above results prove that the diallyl bisphenol A modified bismaleimide resin prepared in Control Example 1 have no replasticity and cannot be reshaped by hot pressing.

Example 2

1) The preparation of 2-allylphenyl glycidyl ether. By mass, the solution A was obtained: 120 g of 2-allylphenol, 100 g of NaOH, 5 g of tetramethylammonium bromide and 200 g of tetrahydrofuran were maintained and stirred at 25° C. for 1 h; and then, 250 g of epichlorohydrin was slowly added into the solution A, which was maintained at 25° C. for 6 h. After the reaction, tetrahydrofuran and epichlorohydrin were removed in vacuum rotary evaporation propane to give a crude product. The crude product was washed with saturated NH$_4$Cl solution (200 ml×2) and deionized water (200 mL×2) successively. Finally separating and purifying by using column chromatography to obtain a yellow viscous liquid which is 2-allylphenyl glycidyl ether (yield was 90.1%).

2) The preparation of bis(3-(2-allylphenoxy)-2-hydroxypropyl) terephthalate. By mass, 120 g of 2-allylphenyl glycidyl ether, 40 g of terephthalic acid, 5 g of tetramethylammonium bromide and 200 g of acetonitrile were maintained and stirred at 65° C. for 8 h. After the reaction, acetonitrile was removed in vacuum rotary evaporation propane to give a crude product. The crude product was washed with saturated NaHCO$_3$ solution (200 ml×2) and deionized water (200 mL×2) successively. Finally separating and purifying by using column chromatography to obtain a yellow oil product which is bis(3-(2-allylphenoxy)-2-hydroxypropyl) terephthalate (yield was 86.4%).

3) The preparation of remoldable bismaleimide resin, N,N'-4,4'-diphenylmethane bismaleimide 50 g (139.5 mmol), bis(3-(2-allylphenoxy)-2-hydroxypropyl) terephthalate 65.52 g (119.97 mmol) and zinc acetylacetonate hydrate 6.67 g (23.99 mmol) and stirred and prepolymerized at 125° C. for 25 min to obtain a clear prepolymer; poured the clarified prepolymer into the preheated mold at 130° C., put it in a vacuum oven at 130° C. and vacuuming for 45 minutes; moved the evacuated prepolymer into a blast drying oven, and solidify according to the following process post-treatment: 160° C./2 h+180° C./2 h+200° C./2 h+220° C./2 h and 240° C./4 h; after natural cooling, demolding, the remoldable bismaleimide resin can be obtained. The T$_{di}$ is 371° C.

4) Remolding method of remoldable bismaleimide resin and remolded bismaleimide resin, pressing down the pulverized remoldable bismaleimide resin at 240° C. and 40 MPa for 8 h; After natural cooling released the mold to obtain the remoldable bismaleimide resin, which realized the remolding of the bismaleimide resin. The surface of the obtained remolded resin block is smooth without cracks, indicating that the resin particles have undergone a dynamic transesterification reaction to reconnect the particles. This result fully proves that the bismaleimide resin can be reshaped by the present invention. After remolding, the repair efficiency of the three parameters of the stensile strength, tensile modulus, and elongation is 83%, 92% and 92%, indicating that the re shaped bismaleimide resin still maintains good tensile properties.

Example 3

1) The preparation of 2-allylphenyl glycidyl ether. By mass, the solution A was obtained: 120 g of 2-allylphenol, 140 g of NaOH, 7.5 g of tetrabutylammonium bromide and 250 g of tetrahydrofuran were maintained and stirred at 35° C. for 1.5 h; and then, 300 g of epichlorohydrin was slowly added into the solution A, which was maintained at 35° C. for 8 h. After the reaction, tetrahydrofuran and epichlorohydrin were removed in vacuum rotary evaporation propane to give a crude product. The crude product was washed with saturated NH$_4$Cl solution (200 ml×2) and deionized water (200 mL×2) successively. Finally separating and purifying by using column chromatography to obtain a yellow viscous liquid which is 2-allylphenyl glycidyl ether (yield was 91.7%).

2) The preparation of bis(3-(2-allylphenoxy)-2-hydroxypropyl) terephthalate. By mass, 120 g of 2-allylphenyl glycidyl ether, 40 g of terephthalic acid, 7.5 g of tetrabutylammonium bromide and 250 g of acetonitrile were maintained and stirred at 75° C. for 10 h. After the reaction, acetonitrile was removed in vacuum rotary evaporation propane to give a crude product. The crude product was washed with saturated NaHCO$_3$ solution (200 ml×2) and deionized water (200 mL×2) successively. Finally separating and purifying by using column chromatography to obtain a yellow oil product which is bis(3-(2-allylphenoxy)-2-hydroxypropyl) terephthalate (yield was 86.2%).

3) The preparation of remoldable bismaleimide resin, N,N'-4,4'-diphenylmethane bismaleimide 50 g (139.5 mmol), bis(3-(2-allylphenoxy)-2-hydroxypropyl) terephthalate 85.31 g (156.24 mmol) and zinc acetylacetonate hydrate 8.23 g (31.35 mmol) and stirred and prepolymerized at 130° C. for 15 min to obtain a clear prepolymer; poured the clarified prepolymer into the preheated mold at 130° C., put it in a vacuum oven at 130° C. and vacuuming for 45 minutes; moved the evacuated prepolymer into a blast drying oven, and solidify according to the following process post-treatment: 160° C./2 h+180° C./2 h+200° C./2 h+220° C./2 h and 240° C./4 h; after natural cooling, demolding, the remoldable bismaleimide resin can be obtained. The T$_{di}$ is 372° C.

4) Remolding method of remoldable bismaleimide resin and remolded bismaleimide resin, pressing down the pulverized remoldable bismaleimide resin at 240° C. and 40 MIPa for 8 h; After natural cooling released the mold to obtain the remoldable bismaleimide resin, which realized the remolding of the bismaleimide resin. The surface of the obtained remolded resin block is smooth without cracks, indicating that the resin particles have undergone a dynamic transesterification reaction to reconnect the particles. This result fully proves that the bismaleimide resin can be reshaped by the present invention. After remolding, the repair efficiency of the three parameters of the stensile strength, tensile modulus, and elongation is 85%, 98% and 87%, indicating that the reshaped bismaleimide resin still maintains good tensile properties.

Example 4

1) The preparation of 2-allylphenyl glycidyl ether. By mass, the solution A was obtained: 120 g of 2-allylphenol, 150 g of NaOH, 10 g of tetrabutylammonium bromide and 300 g of tetrahydrofuran were maintained and stirred at 40° C. for 2 h; and then, 350 g of epichlorohydrin was slowly added into the solution A, which was maintained at 40° C. for 10 h. After the reaction, tetrahydrofuran and epichlorohydrin were removed in vacuum rotary evaporation propane to give a crude product. The crude product was washed with saturated NH$_4$Cl solution (200 ml×2) and deionized water (200 mL×2) successively. Finally separating and purifying by using column chromatography to obtain a yellow viscous liquid which is 2-allylphenyl glycidyl ether (yield was 93.7%).

2) The preparation of bis(3-(2-allylphenoxy)-2-hydroxypropyl) terephthalate. By mass, 120 g of 2-allylphenyl glycidyl ether, 50 g of terephthalic acid, 10 g of tetrabutylammonium bromide and 300 g of acetonitrile were maintained and stirred at 80° C. for 12 h. After the reaction, acetonitrile was removed in vacuum rotary evaporation propane to give a crude product. The crude product was washed with saturated NaHCO$_3$ solution (200 ml×2) and deionized water (200 mL×2) successively. Finally separating and purifying by using column chromatography to obtain a yellow oil product which is bis(3-(2-allylphenoxy)-2-hydroxypropyl) terephthalate (yield was 85.2%).

3) The preparation of remoldable bismaleimide resin, N,N'-(1,4-phenylene) bismaleimide 50 g (186.4 mmol), bis(3-(2-allylphenoxy)-2-hydroxypropyl) terephthalate 87.5 g (160.3 mmol) and zinc acetylacetonate hydrate 9.03 g (32.06 mmol) and stirred and prepolymerized at 130° C. for 18 min to obtain a clear prepolymer; poured the clarified prepolymer into the preheated mold at 130° C., put it in a vacuum oven at 130° C. and vacuuming for 45 minutes; moved the evacuated prepolymer into a blast drying oven, and solidify according to the following process post-treatment: 160° C./2 h+180° C./2 h+200° C./2 h+220° C./2 h and 240° C./4 h; after natural cooling, demolding, the remoldable bismaleimide resin can be obtained.

4) Remolding method of remoldable bismaleimide resin and remolded bismaleimide resin, pressing down the pulverized remoldable bismaleimide resin at 300° C. and 20 MPa for 2 h; After natural cooling released the mold to obtain the remoldable bismaleimide resin, which realized the remolding of the bismaleimide resin. The surface of the obtained remolded resin block is smooth without cracks, indicating that the resin particles have undergone a dynamic transesterification reaction to reconnect the particles. This result fully proves that the bismaleimide resin can be reshaped by the present invention. After remolding, the repair efficiency of the three parameters of the stensile strength, tensile modulus, and elongation is 82%, 97% and 90%, indicating that the reshaped bismaleimide resin still maintains good tensile properties.

Example 5

1) The preparation of 2-allylphenyl glycidyl ether. By mass, the solution A was obtained: 120 g of 2-allylphenol, 130 g of NaOH, 10 g of tetrabutylammonium bromide and 280 g of tetrahydrofuran were maintained and stirred at 30° C. for 2 h; and then, 320 g of epichlorohydrin was slowly added into the solution A, which was maintained at 30° C. for 10 h. After the reaction, tetrahydrofuran and epichlorohydrin were removed in vacuum rotary evaporation propane to give a crude product. The crude product was washed with saturated NH$_4$Cl solution (200 ml×2) and deionized water (200 mL×2) successively. Finally separating and purifying by using column chromatography to obtain a yellow viscous liquid which is 2-allylphenyl glycidyl ether (yield was 92.6%).

2) The preparation of bis(3-(2-allylphenoxy)-2-hydroxypropyl) terephthalate. By mass, 120 g of 2-allylphenyl glycidyl ether, 48 g of terephthalic acid, 10 g of tetrabutylammonium bromide and 300 g of acetonitrile were maintained and stirred at 70° C. for 10 h. After the reaction, acetonitrile was removed in vacuum rotary evaporation propane to give a crude product. The crude product was washed with saturated NaHCO$_3$ solution (200 ml×2) and deionized water (200 mL×2) successively. Finally separating and purifying by using column chromatography to obtain a yellow oil product which is bis(3-(2-allylphenoxy)-2-hydroxypropyl) terephthalate (yield was 84.3%).

3) The preparation of remoldable bismaleimide resin, N,N'-(1,4-phenylene) bismaleimide 50 g (186.4 mmol), bis(3-(2-allylphenoxy)-2-hydroxypropyl) terephthalate 101.78 (186.4 mmol) and zinc acetylacetonate hydrate 10.5 g (37.28 mmol) and stirred and prepolymerized at 135° C. for 15 min to obtain a clear prepolymer; poured the clarified prepolymer into the preheated mold at 130° C., put it in a vacuum oven at 130° C. and vacuuming for 45 minutes; moved the evacuated prepolymer into a blast drying oven, and solidify according to the following process post-treatment: 160° C./2 h+180° C./2 h+200° C./2 h+220° C./2 h and 240° C./4 h; after natural cooling, demolding, the remoldable bismaleimide resin can be obtained.

4) Remolding method of remoldable bismaleimide resin and remolded bismaleimide resin, pressing down the pulverized remoldable bismaleimide resin at 270° C. and 35 MPa for 5 h; After natural cooling released the mold to obtain the remoldable bismaleimide resin, which realized the remolding of the bismaleimide resin. The surface of the obtained remolded resin block is smooth without cracks, indicating that the resin particles have undergone a dynamic transesterification reaction to reconnect the particles. This result fully proves that the bismaleimide resin can be reshaped by the present invention. After remolding, the repair efficiency of the three parameters of the stensile strength, tensile modulus, and elongation is 85%, 93% and 91%, indicating that the reshaped bismaleimide resin still maintains good tensile properties.

Example 6

1) The preparation of 2-allylphenyl glycidyl ether. By mass, the solution A was obtained: 120 g of 2-allylphenol, 130 g of NaOH, 6 g of tetramethylammonium bromide and 280 g of tetrahydrofuran were maintained and stirred at 30° C. for 2 h; and then, 320 g of epichlorohydrin was slowly added into the solution A, which was maintained at 30° C. for 10 h. After the reaction, tetrahydrofuran and epichlorohydrin were removed in vacuum rotary evaporation propane to give a crude product. The crude product was washed with saturated NH$_4$Cl solution (200 ml×2) and deionized water (200 mL×2) successively. Finally separating and purifying by using column chromatography to obtain a yellow viscous liquid which is 2-allylphenyl glycidyl ether (yield was 90.6%).

2) The preparation of bis(3-(2-allylphenoxy)-2-hydroxypropyl) terephthalate. By mass, 120 g of 2-allylphenyl glycidyl ether, 48 g of terephthalic acid, 6 g of tetramethylammonium bromide and 280 g of acetonitrile were maintained and stirred at 68° C. for 10 h. After the reaction, acetonitrile was removed in vacuum rotary evaporation propane to give a crude product. The crude product was washed with saturated NaHCO$_3$ solution (200 ml×2) and deionized water (200 mL×2) successively. Finally separating and purifying by using column chromatography to obtain a yellow oil product which is bis(3-(2-allylphenoxy)-2-hydroxypropyl) terephthalate (yield was 83.7%).

3) The preparation of remoldable bismaleimide resin, N,N'-(1,4-phenylene) bismaleimide 50 g (186.4 mmol), bis(3-(2-allylphenoxy)-2-hydroxypropyl) terephthalate 114 g (208.08 mmol) and zinc acetylacetonate hydrate 11.76 g (41.76 mmol) and stirred and prepolymerized at 120° C. for 2 5 min to obtain a clear prepolymer; poured the clarified prepolymer into the preheated mold at 130° C., put it in a vacuum oven at 130° C. and vacuuming for 45 minutes; moved the evacuated prepolymer into a blast drying oven, and solidify according to the following process post-treatment: 160° C./2 h+180° C./2 h+200° C./2 h+220° C./2 h and 240° C./4 h; after natural cooling, demolding, the remoldable bismaleimide resin can be obtained.

4) Remolding method of remoldable bismaleimide resin and remolded bismaleimide resin, pressing down the pulverized remoldable bismaleimide resin at 270° C. and 32 MPa for 6 h; After natural cooling released the mold to obtain the remoldable bismaleimide resin, which realized the remolding of the bismaleimide resin. The surface of the obtained remolded resin block is smooth without cracks, indicating that the resin particles have undergone a dynamic transesterification reaction to reconnect the particles. This result fully proves that the bismaleimide resin can be reshaped by the present invention.

Example 7

1) The preparation of 2-allylphenyl glycidyl ether. By mass, the solution A was obtained: 120 g of 2-allylphenol, 140 g of NaOH, 2 g of tetramethylammonium bromide, 6 g of tetrabutylammonium bromide and 280 g of tetrahydrofuran were maintained and stirred at 40° C. for 2 h; and then, 330 g of epichlorohydrin was slowly added into the solution A, which was maintained at 40° C. for 10 h. After the reaction, tetrahydrofuran and epichlorohydrin were removed in vacuum rotary evaporation propane to give a crude product. The crude product was washed with saturated NH$_4$Cl solution (200 ml×2) and deionized water (200 mL×2) successively. Finally separating and purifying by using column chromatography to obtain a yellow viscous liquid which is 2-allylphenyl glycidyl ether (yield was 91.7%).

2) The preparation of bis(3-(2-allylphenoxy)-2-hydroxypropyl) terephthalate. By mass, 120 g of 2-allylphenyl glycidyl ether, 48 g of terephthalic acid, 2 g of tetramethylammonium bromide, 6 g of tetrabutylammonium bromide and 280 g of acetonitrile were maintained and stirred at 72° C. for 12 h. After the reaction, acetonitrile was removed in vacuum rotary evaporation propane to give a crude product. The crude product was washed with saturated NaHCO$_3$ solution (200 ml×2) and deionized water (200 mL×2) successively. Finally separating and purifying by using column chromatography to obtain a yellow oil product which is bis(3-(2-allylphenoxy)-2-hydroxypropyl) terephthalate (yield was 86.1%).

3) The preparation of remoldable bismaleimide resin, N,N'-m-phenylene bismaleimide 50 g (186.4 mmol), bis(3-(2-allylphenoxy)-2-hydroxypropyl) terephthalate 87.5 g (160.3 mmol) and zinc acetylacetonate hydrate 9.03 g (32.06 mmol) and stirred and prepolymerized at 127° C. for 22 min to obtain a clear prepolymer; poured the clarified prepolymer into the preheated mold at 130° C., put it in a vacuum oven at 130° C. and vacuuming for 45 minutes; moved the evacuated prepolymer into a blast drying oven, and solidify according to the following process post-treatment: 160° C./2 h+180° C./2 h+200° C./2 h+220° C./2 h and 240° C./4 h; after natural cooling, demolding, the remoldable bismaleimide resin can be obtained.

4) Remolding method of remoldable bismaleimide resin and remolded bismaleimide resin, pressing down the pulverized remoldable bismaleimide resin at 260° C. and 35 MPa for 6 h; After natural cooling released the mold to obtain the remoldable bismaleimide resin, which realized the remolding of the bismaleimide resin. The surface of the obtained remolded resin block is smooth without cracks, indicating that the resin particles have undergone a dynamic transesterification reaction to reconnect the particles. This result fully proves that the bismaleimide resin can be reshaped by the present invention.

Example 8

1) The preparation of 2-allylphenyl glycidyl ether. By mass, the solution A was obtained: 120 g of 2-allylphenol, 140 g of NaOH, 2 g of tetramethylammonium bromide, 7 g of tetrabutylammonium bromide and 260 g of tetrahydrofuran were maintained and stirred at 25° C. for 1.5 h; and then, 310 g of epichlorohydrin was slowly added into the solution A, which was maintained at 25° C. for 10 h. After the reaction, tetrahydrofuran and epichlorohydrin were removed in vacuum rotary evaporation propane to give a crude product. The crude product was washed with saturated NH$_4$Cl solution (200 ml×2) and deionized water (200 mL×2) successively. Finally separating and purifying by using column chromatography to obtain a yellow viscous liquid which is 2-allylphenyl glycidyl ether (yield was 90.5%).

2) The preparation of bis(3-(2-allylphenoxy)-2-hydroxypropyl) terephthalate. By mass, 120 g of 2-allylphenyl glycidyl ether, 42 g of terephthalic acid, 2 g of tetramethylammonium bromide, 7 g of tetrabutylammonium bromide and 260 g of acetonitrile were maintained and stirred at 78° C. for 10 h. After the reaction, acetonitrile was removed in vacuum rotary evaporation propane to give a crude product. The crude product was washed with saturated NaHCO$_3$ solution (200 ml×2) and deionized water (200 mL×2) successively. Finally separating and purifying by using column chromatography to obtain a yellow oil product which is bis(3-(2-allylphenoxy)-2-hydroxypropyl) terephthalate (yield was 84.9%). 3) The preparation of remoldable bismaleimide resin, N,N'-m-phenylene bismaleimide 50 g (186.4 mmol), bis(3-(2-allylphenoxy)-2-hydroxypropyl) terephthalate 101.78 g (186.4 mmol) and zinc acetylacetonate hydrate 10.5 g (37.28 mmol) and stirred and prepolymerized at 135° C. for 15 min to obtain a clear prepolymer; poured the clarified prepolymer into the preheated mold at 130° C., put it in a vacuum oven at 130° C. and vacuuming for 45 minutes; moved the evacuated prepolymer into a blast drying oven, and solidify according to the following process post-treatment: 160° C./2 h+180° C./2 h+200° C./2 h+220° C./2 h and 240° C./4 h; after natural cooling, demolding, the remoldable bismaleimide resin can be obtained.

4) Remolding method of remoldable bismaleimide resin and remolded bismaleimide resin, pressing down the pulverized remoldable bismaleimide resin at 250° C. and 40 MPa for 7 h; After natural cooling released the mold to obtain the remoldable bismaleimide resin, which realized the remolding of the bismaleimide resin. The surface of the obtained remolded resin block is smooth without cracks, indicating that the resin particles have undergone a dynamic transesterification reaction to reconnect the particles. This result fully proves that the bismaleimide resin can be reshaped by the present invention.

Example 9

1) The preparation of 2-allylphenyl glycidyl ether. By mass, the solution A was obtained: 120 g of 2-allylphenol, 140 g of NaOH, 3 g of tetramethylammonium bromide, 5 g of tetrabutylammonium bromide and 200 g of tetrahydrofuran were maintained and stirred at 28° C. for 1 h; and then, 250 g of epichlorohydrin was slowly added into the solution A, which was maintained at 28° C. for 10 h. After the reaction, tetrahydrofuran and epichlorohydrin were removed in vacuum rotary evaporation propane to give a crude product. The crude product was washed with saturated $NH_4Cl$ solution (200 ml×2) and deionized water (200 mL×2) successively. Finally separating and purifying by using column chromatography to obtain a yellow viscous liquid which is 2-allylphenyl glycidyl ether (yield was 90.1%).

2) The preparation of bis(3-(2-allylphenoxy)-2-hydroxypropyl) terephthalate. By mass, 120 g of 2-allylphenyl glycidyl ether, 40 g of terephthalic acid, 3 g of tetramethylammonium bromide, 5 g of tetrabutylammonium bromide and 200 g of acetonitrile were maintained and stirred at 65° C. for 12 h. After the reaction, acetonitrile was removed in vacuum rotary evaporation propane to give a crude product. The crude product was washed with saturated $NaHCO_3$ solution (200 ml×2) and deionized water (200 mL×2) successively. Finally separating and purifying by using column chromatography to obtain a yellow oil product which is bis(3-(2-allylphenoxy)-2-hydroxypropyl) terephthalate (yield was 85.8%).

3) The preparation of remoldable bismaleimide resin, N,N'-m-phenylene bismaleimide 50 g (186.4 mmol), bis(3-(2-allylphenoxy)-2-hydroxypropyl) terephthalate 114 g (208.08 mmol) and zinc acetylacetonate hydrate 11.76 g (41.76 mmol) and stirred and prepolymerized at 120° C. for 25 min to obtain a clear prepolymer; poured the clarified prepolymer into the preheated mold at 130° C., put it in a vacuum oven at 130° C. and vacuuming for 45 minutes; moved the evacuated prepolymer into a blast drying oven, and solidify according to the following process post-treatment: 160° C./2 h+180° C./2 h+200° C./2 h+220° C./2 h and 240° C./4 h; after natural cooling, demolding, the remoldable bismaleimide resin can be obtained.

4) Remolding method of remoldable bismaleimide resin and remolded bismaleimide resin, pressing down the pulverized remoldable bismaleimide resin at 280° C. and 20 MIPa for 5 h; After natural cooling released the mold to obtain the remoldable bismaleimide resin, which realized the remolding of the bismaleimide resin. The surface of the obtained remolded resin block is smooth without cracks, indicating that the resin particles have undergone a dynamic transesterification reaction to reconnect the particles. This result fully proves that the bismaleimide resin can be reshaped by the present invention.

Example 10

1) The preparation of 2-allylphenyl glycidyl ether. By mass, the solution A was obtained: 120 g of 2-allylphenol, 140 g of NaOH, 7 g of tetramethylammonium bromide, 3 g of tetrabutylammonium bromide and 270 g of tetrahydrofuran were maintained and stirred at 33° C. for 2 h; and then, 320 g of epichlorohydrin was slowly added into the solution A, which was maintained at 33° C. for 8 h. After the reaction, tetrahydrofuran and epichlorohydrin were removed in vacuum rotary evaporation propane to give a crude product. The crude product was washed with saturated $NH_4Cl$ solution (200 ml×2) and deionized water (200 mL×2) successively. Finally separating and purifying by using column chromatography to obtain a yellow viscous liquid which is 2-allylphenyl glycidyl ether (yield was 90.5%).

2) The preparation of bis(3-(2-allylphenoxy)-2-hydroxypropyl) terephthalate. By mass, 120 g of 2-allylphenyl glycidyl ether, 46 g of terephthalic acid, 7 g of tetramethylammonium bromide, 2 g of tetrabutylammonium bromide and 290 g of acetonitrile were maintained and stirred at 70° C. for 8 h. After the reaction, acetonitrile was removed in vacuum rotary evaporation propane to give a crude product. The crude product was washed with saturated $NaHCO_3$ solution (200 ml×2) and deionized water (200 mL×2) successively. Finally separating and purifying by using column chromatography to obtain a yellow oil product which is bis(3-(2-allylphenoxy)-2-hydroxypropyl) terephthalate (yield was 82.9%).

3) The preparation of remoldable bismaleimide resin, N,N'-4,4'-diphenylmethane bismaleimide 25 g (69.75 mmol), N,N'-m-phenylene bismaleimide 25 g (93.2 mmol), bis(3-(2-allylphenoxy)-2-hydroxypropyl) terephthalate 76.51 g (140.14 mmol) and zinc acetylacetonate hydrate 7.89 g (28.02 mmol) and stirred and prepolymerized at 125° C. for 20 min to obtain a clear prepolymer; poured the clarified prepolymer into the preheated mold at 130° C., put it in a vacuum oven at 130° C. and vacuuming for 45 minutes; moved the evacuated prepolymer into a blast drying oven, and solidify according to the following process post-treatment: 160° C./2 h+180° C./2 h+200° C./2 h+220° C./2 h and 240° C./4 h; after natural cooling, demolding, the remoldable bismaleimide resin can be obtained.

4) Remolding method of remoldable bismaleimide resin and remolded bismaleimide resin, pressing down the pulverized remoldable bismaleimide resin at 270° C. and 30 MPa for 5 h; After natural cooling released the mold to obtain the remoldable bismaleimide resin, which realized the remolding of the bismaleimide resin. The surface of the obtained remolded resin block is smooth without cracks, indicating that the resin particles have undergone a dynamic transesterification reaction to reconnect the particles. This result fully proves that the bismaleimide resin can be reshaped by the present invention.

Example 11

1) The preparation of 2-allylphenyl glycidyl ether. By mass, the solution A was obtained: 120 g of 2-allylphenol, 120 g of NaOH, 5 g of tetramethylammonium bromide, 5 g of tetrabutylammonium bromide and 250 g of tetrahydrofuran were maintained and stirred at 37° C. for 2 h; and then, 300 g of epichlorohydrin was slowly added into the solution A, which was maintained at 37° C. for 9 h. After the reaction, tetrahydrofuran and epichlorohydrin were removed in vacuum rotary evaporation propane to give a crude product. The crude product was washed with saturated $NH_4Cl$ solution (200 ml×2) and deionized water (200 mL×2) successively. Finally separating and purifying by using column chromatography to obtain a yellow viscous liquid which is 2-allylphenyl glycidyl ether (yield was 92.4%).

2) The preparation of bis(3-(2-allylphenoxy)-2-hydroxypropyl) terephthalate. By mass, 120 g of 2-allylphenyl glycidyl ether, 42 g of terephthalic acid, 5 g of tetramethylammonium bromide, 5 g of tetrabutylammonium bromide and 260 g of acetonitrile were maintained and stirred at 75° C. for 9 h. After the reaction, acetonitrile was removed in vacuum rotary evaporation propane to give a crude product. The crude product was washed with saturated $NaHCO_3$ solution (200 ml×2) and deionized water (200 mL×2) successively. Finally separating and purifying by using column chromatography to obtain a yellow oil product which is bis(3-(2-allylphenoxy)-2-hydroxypropyl) terephthalate (yield was 85.2%).

3) The preparation of remoldable bismaleimide resin, N,N'-m-phenylene bismaleimide 25 g (93.2 mmol), N,N'-

(1,4-phenylene) bismaleimide 25 g (93.2 mmol), bis(3-(2-allylphenoxy)-2-hydroxypropyl) terephthalate 101.78 g (186.4 mmol) and zinc acetylacetonate hydrate 10.5 g (37.28 mmol) and stirred and prepolymerized at 128° C. for 19 min to obtain a clear prepolymer; poured the clarified prepolymer into the preheated mold at 130° C., put it in a vacuum oven at 130° C. and vacuuming for 45 minutes; moved the evacuated prepolymer into a blast drying oven, and solidify according to the following process post-treatment: 160° C./2 h+180° C./2 h+200° C./2 h+220° C./2 h and 240° C./4 h; after natural cooling, demolding, the remoldable bismaleimide resin can be obtained.

4) Remolding method of remoldable bismaleimide resin and remolded bismaleimide resin, pressing down the pulverized remoldable bismaleimide resin at 240° C. and 40 MPa for 7 h; After natural cooling released the mold to obtain the remoldable bismaleimide resin, which realized the remolding of the bismaleimide resin. The surface of the obtained remolded resin block is smooth without cracks, indicating that the resin particles have undergone a dynamic transesterification reaction to reconnect the particles. This result fully proves that the bismaleimide resin can be reshaped by the present invention.

Example 12

1) The preparation of 2-allylphenyl glycidyl ether. By mass, the solution A was obtained: 120 g of 2-allylphenol, 130 g of NaOH, 7.5 g of tetrabutylammonium bromide and 250 g of tetrahydrofuran were maintained and stirred at 30° C. for 1.2 h; and then, 300 g of epichlorohydrin was slowly added into the solution A, which was maintained at 30° C. for 7.5 h. After the reaction, tetrahydrofuran and epichlorohydrin were removed in vacuum rotary evaporation propane to give a crude product. The crude product was washed with saturated $NH_4Cl$ solution (200 mL×2) and deionized water (200 mL×2) successively. Finally separating and purifying by using column chromatography to obtain a yellow viscous liquid which is 2-allylphenyl glycidyl ether (yield was 92.7%).

2) The preparation of bis(3-(2-allylphenoxy)-2-hydroxypropyl) terephthalate. By mass, 120 g of 2-allylphenyl glycidyl ether, 45 g of terephthalic acid, 8 g of tetrabutylammonium bromide and 250 g of acetonitrile were maintained and stirred at 80° C. for 9.5 h. After the reaction, acetonitrile was removed in vacuum rotary evaporation propane to give a crude product. The crude product was washed with saturated $NaHCO_3$ solution (200 mL×2) and deionized water (200 mL×2) successively. Finally separating and purifying by using column chromatography to obtain a yellow oil product which is bis(3-(2-allylphenoxy)-2-hydroxypropyl) terephthalate (yield was 86.7%).

3) The preparation of remoldable bismaleimide resin, N,N'-4,4'-diphenylmethane bismaleimide 25 g (69.75 mmol), N,N'-m-phenylene bismaleimide 12.5 g (46.6 mmol), N,N'-(1,4-phenylene) bismaleimide 12.5 g (46.6 mmol), bis(3-(2-allylphenoxy)-2-hydroxypropyl) terephthalate 88.97 g (162.95 mmol) and zinc acetylacetonate hydrate 10.28 g (36.5 mmol) and stirred and prepolymerized at 132° C. for 20 min to obtain a clear prepolymer; poured the clarified prepolymer into the preheated mold at 130° C., put it in a vacuum oven at 130° C. and vacuuming for 45 minutes; moved the evacuated prepolymer into a blast drying oven, and solidify according to the following process post-treatment: 160° C./2 h+180° C./2 h+200° C./2 h+220° C./2 h and 240° C./4 h; after natural cooling, demolding, the remoldable bismaleimide resin can be obtained.

4) Remolding method of remoldable bismaleimide resin and remolded bismaleimide resin, pressing down the pulverized remoldable bismaleimide resin at 240° C. and 40 MIPa for 6 h; After natural cooling released the mold to obtain the remoldable bismaleimide resin, which realized the remolding of the bismaleimide resin. The surface of the obtained remolded resin block is smooth without cracks, indicating that the resin particles have undergone a dynamic transesterification reaction to reconnect the particles. This result fully proves that the bismaleimide resin can be reshaped by the present invention.

The invention claimed is:

1. A remoldable bismaleimide resin, wherein a preparation method of the remoldable bismaleimide resin comprises the following steps:
   (1) in the presence of a quaternary ammonium salt, reacting 2-allylphenyl glycidyl ether and terephthalic acid to prepare bis(3-(2-allylphenoxy)-2-hydroxypropyl) terephthalate;
   (2) mixing bis(3-(2-allylphenoxy)-2-hydroxypropyl) terephthalate, bismaleimide, and a zinc compound to obtain a remoldable bismaleimide resin system;
   (3) curing and post-treating the remoldable bismaleimide resin system to prepare the remoldable bismaleimide resin.

2. The remoldable bismaleimide resin of claim 1, wherein the 2-allylphenyl glycidyl ether is prepared by adding epichlorohydrin to a mixture of 2-allylphenol, sodium hydroxide, the quaternary ammonium salt, and tetrahydrofuran.

3. The remoldable bismaleimide resin of claim 1, wherein, in the step (1), a mass ratio of 2-allylphenyl glycidyl ether, terephthalic acid and quaternary ammonium salt is 120:40-50:5-10, a reaction temperature is 65-80° C., and a reaction time is 8-12 h; in the step (2), a mass ratio of bismaleimide, bis(3-(2-allylphenoxy)-2-hydroxypropyl) terephthalate and the zinc compound is 50:65.5-114:6.76-11.76, a stirring temperature is 120-135° C., and a reacting time is for 15-25 min; in the step (3), the remoldable bismaleimide resin system is cured and post-treated by casting.

4. The remoldable bismaleimide resin of claim 1, wherein the quaternary ammonium salt is tetramethylammonium bromide or tetrabutylammonium bromide; the zinc compound is zinc acetylacetonate hydrate; the bismaleimide is one or more selected from the group consisting of N,N'-4,4'-diphenylmethane bismaleimide, N,N'-(1,4-phenylene) bismaleimide and N,N'-m-phenylene bismaleimide.

5. The remoldable bismaleimide resin of claim 1, which is used in the preparation of remoldable materials or remoldable thermosetting resins.

6. A method for remolding a bismaleimide resin comprising the following steps:
   (1) in the presence of a quaternary ammonium salt, reacting 2-allylphenyl glycidyl ether and terephthalic acid to prepare bis(3-(2-allylphenoxy)-2-hydroxypropyl) terephthalate;
   (2) mixing bis(3-(2-allylphenoxy)-2-hydroxypropyl) terephthalate, bismaleimide, and a zinc compound to obtain a remoldable bismaleimide resin system;
   (3) curing and post-treating the remoldable bismaleimide resin system to prepare the remoldable bismaleimide resin;
   (4) pulverizing and hot-pressing treating the remoldable bismaleimide resin to a remolded bismaleimide resin, realizing the remolding of the bismaleimide resin.

7. The method for remolding a bismaleimide resin of claim 6, wherein, in the step (1), a mass ratio of 2-allylphenyl glycidyl ether, terephthalic acid and the quaternary ammonium salt is 120: 40-50:5-10, a reaction temperature is 65-80° C. and a reaction time is for 8-12 h; in the step (2), a mass ratio of bismaleimide, bis(3-(2-allylphenoxy)-2-hydroxypropyl) terephthalate and the zinc compound is 50:65.5-114:6.76-11.76, a stirring temperature is 120-135° C., and a reaction time is 15-25 min; in the step (3), the remoldable bismaleimide resin system is cured and post-treated by casting; in the step (4), a temperature of hot pressing treatment is 240-300° C., a pressure is 20-40 MlPa and a reaction time is 2-8 h.

8. The method for remolding a bismaleimide resin of claim 6, wherein the quaternary ammonium salt is tetramethylammonium bromide and/or tetrabutylammonium bromide; the zinc compound is zinc acetylacetonate hydrate; the bismaleimide is one or more selected from the group consisting of N,N'-4,4'-diphenylmethane bismaleimide, N,N'-(1,4-phenylene) bismaleimide, and N,N'-m-phenylene bismaleimide.

9. A remolded bismaleimide resin, wherein a preparation method of the remolded bismaleimide resin comprising the following steps: pulverizing and hot-pressing treating a remoldable bismaleimide resin to obtain the remolded bismaleimide resin; the remoldable bismaleimide resin is from claim 1.

10. The remolded bismaleimide resin of claim 9, wherein a temperature of hot-pressing treatment is 240-300° C., a pressure is 20-40 MPa and a reaction time is 2-8 h.

* * * * *